US008251679B2

(12) United States Patent
Kuehner et al.

(10) Patent No.: US 8,251,679 B2
(45) Date of Patent: Aug. 28, 2012

(54) MEDICAL PUMP

(75) Inventors: Ralf Kuehner, Stuttgart (DE); Lothar Mitzlaff, Lagos (PT); Hans-Jürgen Wahl, Trochtelfingen (DE); Steffen Bauer, Stuttgart (DE)

(73) Assignee: Erbe Elektromedizin GmbH, Tübingen (DE)

( * ) Notice: Subject to any disclaimer, the term of this patent is extended or adjusted under 35 U.S.C. 154(b) by 609 days.

(21) Appl. No.: 12/514,888

(22) PCT Filed: Nov. 13, 2007

(86) PCT No.: PCT/EP2007/009807
§ 371 (c)(1),
(2), (4) Date: Jun. 5, 2009

(87) PCT Pub. No.: WO2008/058704
PCT Pub. Date: May 22, 2008

(65) Prior Publication Data
US 2010/0049228 A1     Feb. 25, 2010

(30) Foreign Application Priority Data
Nov. 14, 2006    (DE) ................... 10 2006 053 609

(51) Int. Cl.
*F04B 35/04*     (2006.01)
(52) U.S. Cl. ............... 417/413.1; 417/415; 604/154
(58) Field of Classification Search .......... 417/413.1, 417/415; 604/154
See application file for complete search history.

(56) References Cited

U.S. PATENT DOCUMENTS

| | | | |
|---|---|---|---|
| 6,216,573 B1 | 4/2001 | Moutafis et al. | |
| 2002/0165491 A1* | 11/2002 | Reilly | 604/154 |
| 2005/0220639 A1* | 10/2005 | Sasaki et al. | 417/415 |
| 2006/0025727 A1 | 2/2006 | Boehringer et al. | |
| 2007/0276421 A1 | 11/2007 | Pein | |
| 2008/0038124 A1* | 2/2008 | Kuehner et al. | 417/413.1 |

FOREIGN PATENT DOCUMENTS

| | | |
|---|---|---|
| DE | 203 09 616 U1 | 11/2003 |
| DE | 10 2004 031 674 B3 | 8/2005 |
| EP | 1 484 071 A1 | 12/2004 |
| EP | 1 588 729 A1 | 10/2005 |
| WO | WO-01/37905 A2 | 5/2001 |
| WO | WO-2006/002815 A1 | 1/2006 |

OTHER PUBLICATIONS

International search Report for PCT/EP2007/009807 (Apr. 18, 2008).
Written Opinion of the International Searching Authority for PCT/EP2007/009807 (in German) (Apr. 18, 2008).
German Examination Report (Aug. 28, 2007).

* cited by examiner

*Primary Examiner* — Charles Freay
*Assistant Examiner* — Patrick Hamo
(74) *Attorney, Agent, or Firm* — Dickstein Shapiro LLP

(57) ABSTRACT

A medical pump for use in water jet surgery which provides ease of connection between a pump unit and a pump actuating device. The medical pump includes a pump unit and a pump actuating device. The pump unit has at least one piston. The pump actuating device includes a holding device and at least one coupling device, the combination of which is configured to connect the pump unit and pistons to the pump actuating device. The pump actuating device includes a drive device controlled by a control system to actuate the pump unit, to open/close the holding device, and to open/close the at least one coupling device. The pump actuating device includes a detection device in communication with the control system that detects a relative position between the pump unit and the pump actuating device and transmits detection signals to the control system.

21 Claims, 26 Drawing Sheets

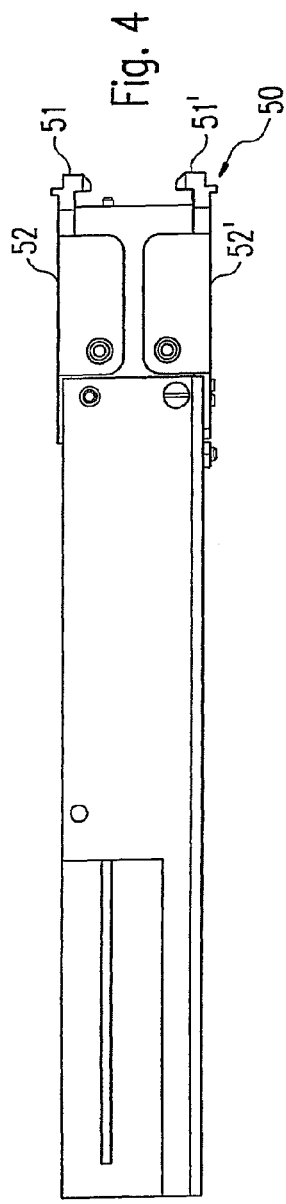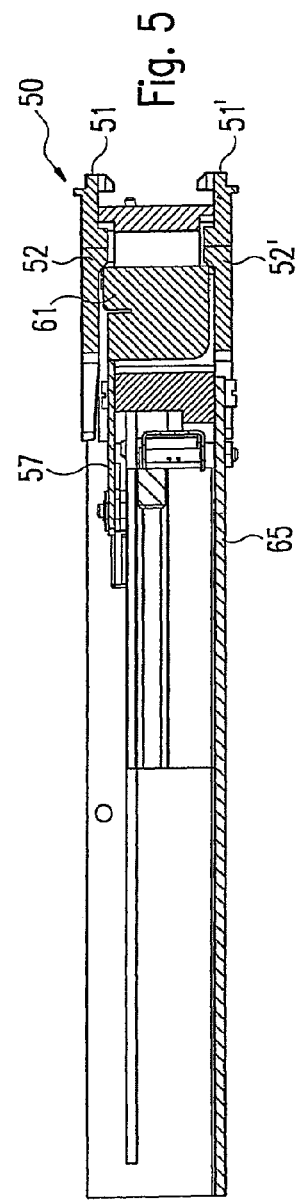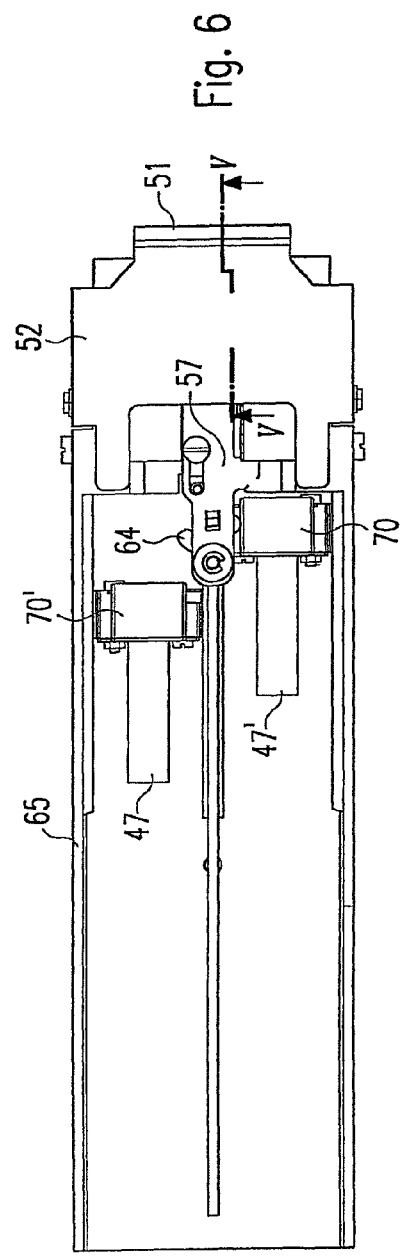

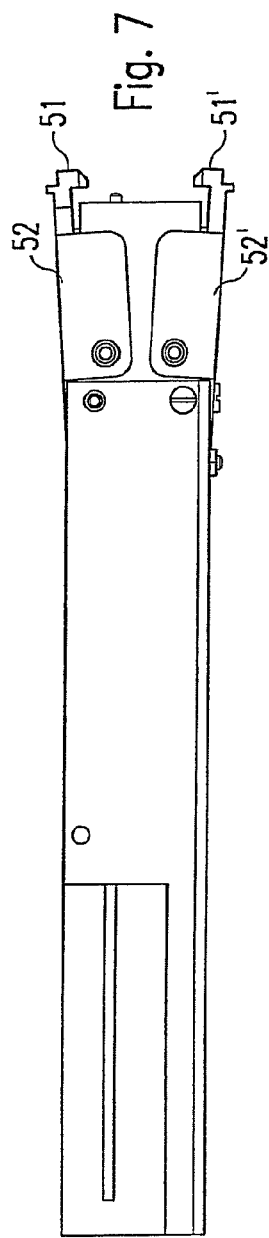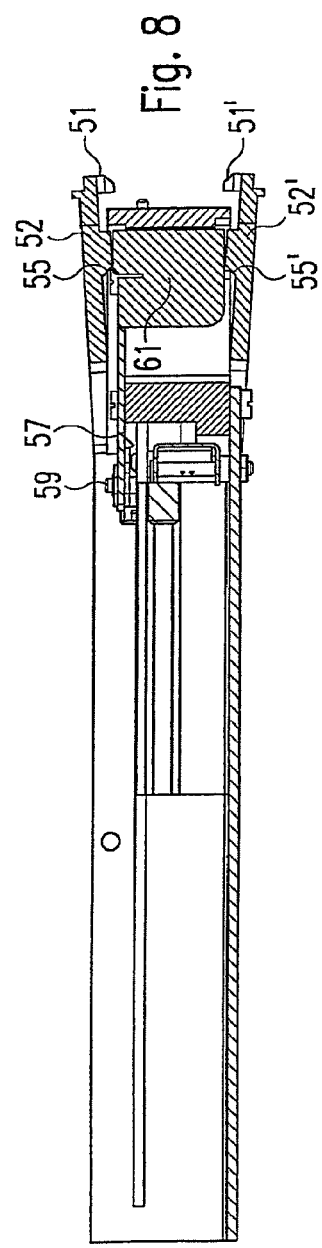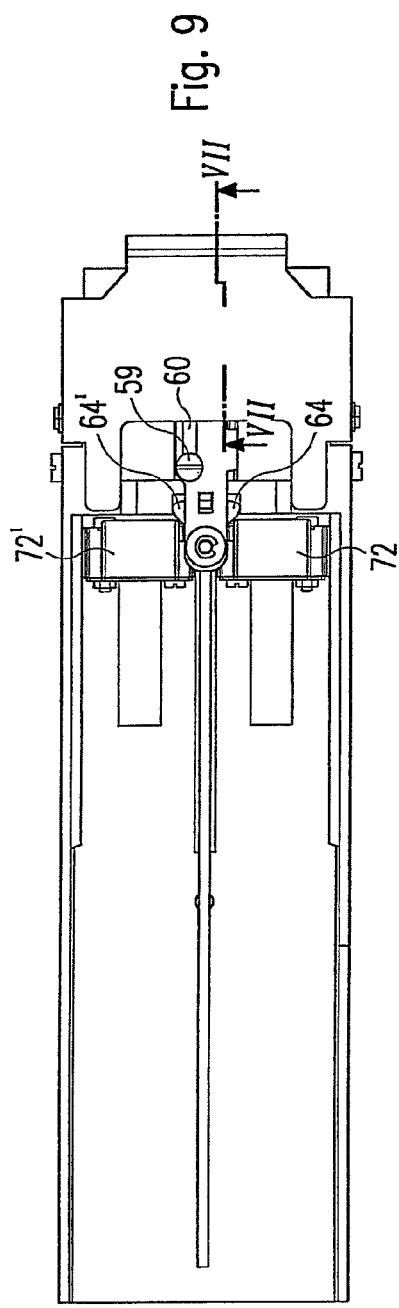

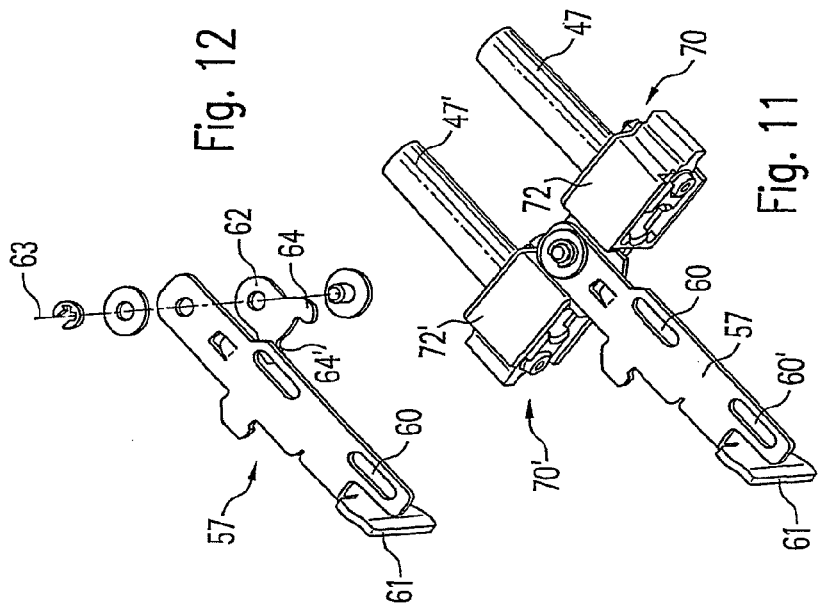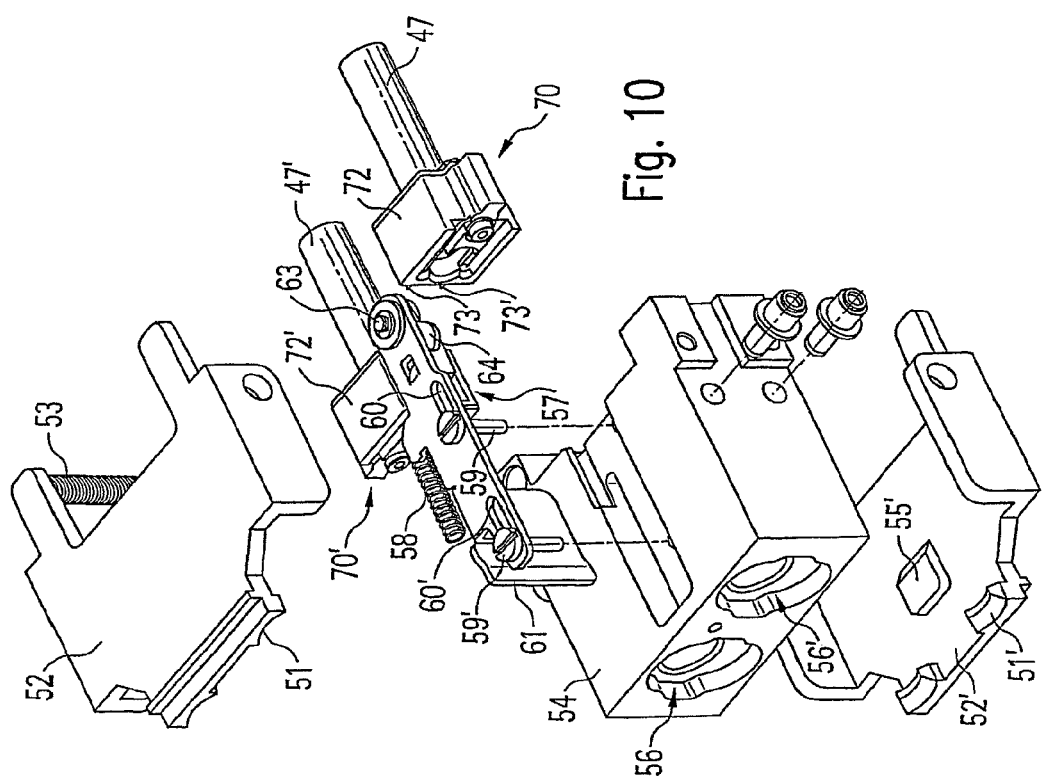

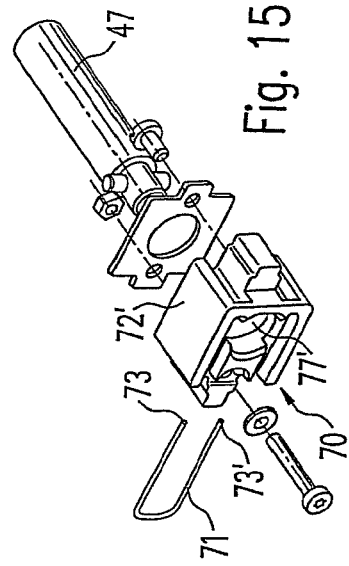
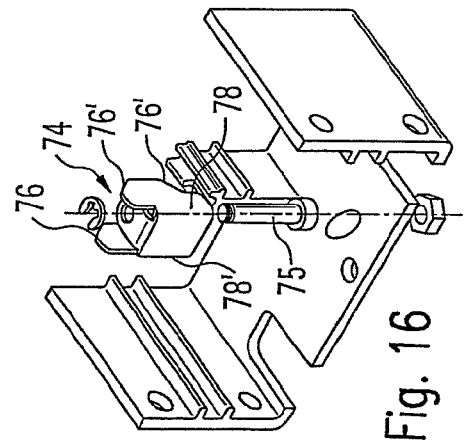
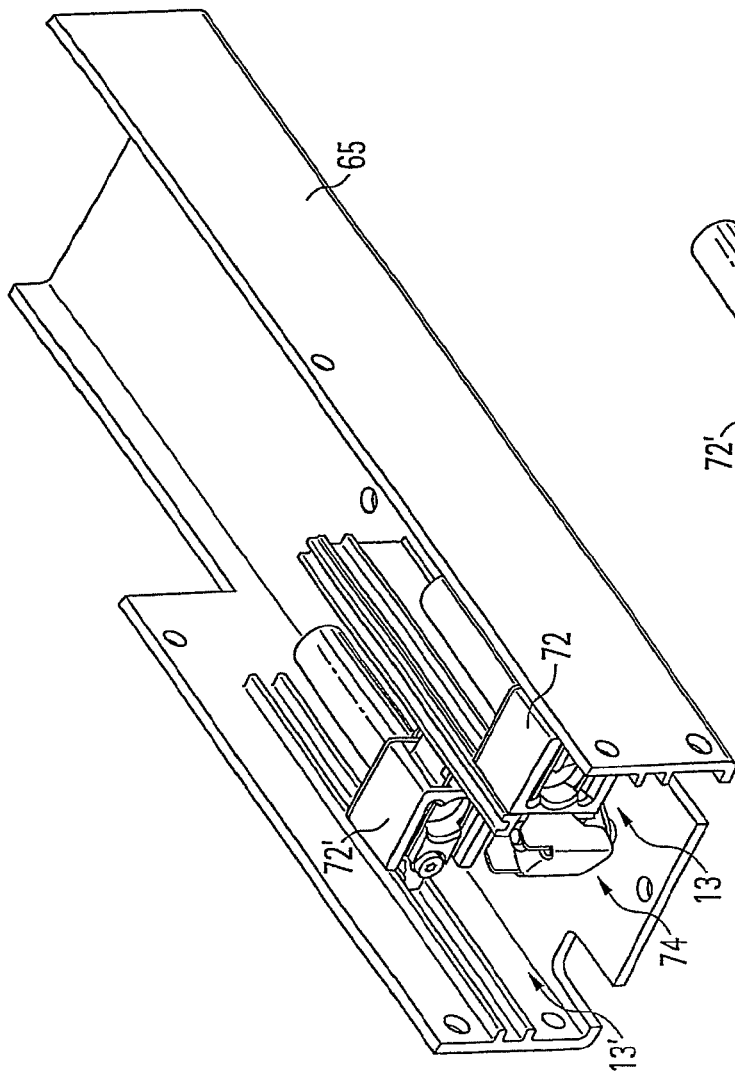
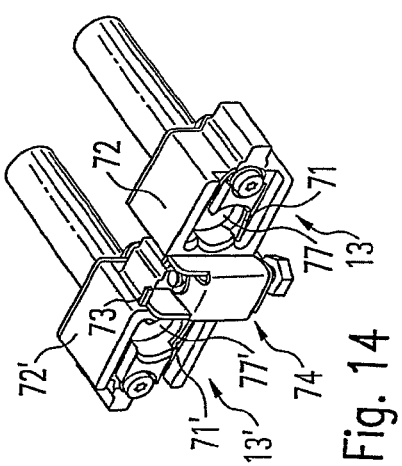

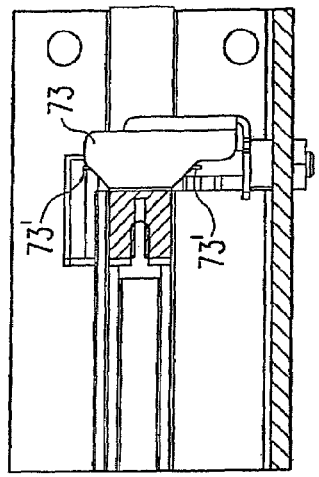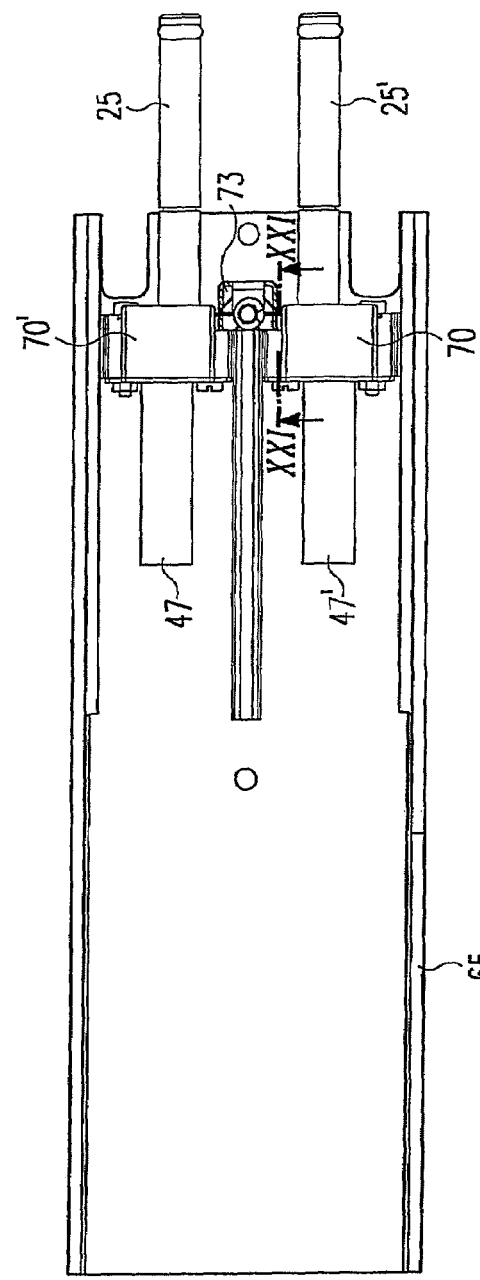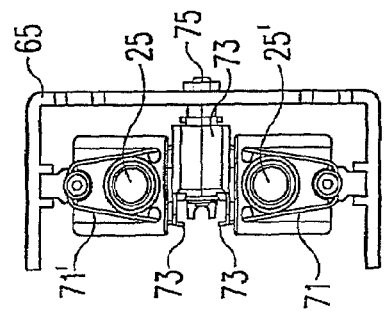

MEDICAL PUMP

FIELD OF INVENTION

The disclosed embodiments relate to a medical pump, in particular for use in water jet surgery.

BACKGROUND

For some time, water jet surgery has been used, for example, in hepatic (liver) surgery since this organ, unlike any other, has tissue structures of varying consistency (parenchyma, blood vessels, bile ducts). Although the water jet separates the tissue to be cut (parenchyma), it leaves the blood vessels and bile ducts undamaged. Of course, this requires precision control of the cutting jet and also of the cutting pressure.

Moreover, care must be taken in water jet surgery to ensure absolute sterility of the cutting medium (e.g. Ringer's solution) since the fluid comes into the closest and most intense contact with the body's tissue. For example, it should be possible to replace exchangeable parts in the easiest manner possible in order to guarantee absolute sterility. Beyond this, of course, attention must also be paid to the usual problems regarding a high level of reliability, simplicity and cost-effective manufacture.

U.S. Pat. No. 6,216,573 B1 and DE 203 09 616 U1 disclose medical pumps for water jet surgery having replaceable pump units, thus designed for single use, which may be coupled to pump actuating devices. However, replacement of the pump devices or pump units is very time-consuming. Since relatively large forces are required to generate a high pressure at adequate flow rates, the devices for coupling the pump device to the pump actuating devices must be of a very sturdy design and have the pump device "firmly under control."

The object of the disclosed embodiments is to develop a medical pump for water jet surgery such that the connection between the pumps unit or pump unit and the pump actuating device is improved and its operability made easier.

SUMMARY

Disclosed embodiments relate to a medical pump, particularly for use in water jet surgery, including a pump unit comprising at least one piston to be displaced in an associated cylinder; and a pump actuating device, that includes an openable and closable holding device for attaching or detaching the pump unit to or from the pump actuating device; openable and closable coupling devices for coupling or uncoupling the pistons to and from the pump actuating device; at least one drive device and a control system for actuating the pump unit by displacing the piston, the drive device being designed in a controllable manner for actuating, particularly opening and/or closing, the holding device and/or the coupling devices in such a way that a working state or idle state is generated; and a detection means, which is connected to an input of the control system in a communicative manner and is embodied in such a way that it detects an insertion state defining a predetermined relative position between the pump unit and the pump actuating device and transmits a first detection signal, describing the presence of the pump unit in the pump actuating device, to the control system for controlling the drive device; the control system for processing the first detection signal being embodied in such a way that it controls the drive device for generating the working state.

The drive device, which is provided for pushing the piston backwards and forwards also actuates or controls the holding devices and/or the coupling devices. Attaching and detaching of the pump unit to or from the pump actuating device and coupling or uncoupling of the pistons to or from the pump actuating device are initiated at least in part due to the detection of the relative position between the pump unit and the pump actuating device. In this case, an operator only needs to insert the pump unit into the holding device with a small amount of force for it already to be retained at least in part by the holding device. Complete, attaching or coupling to the pump actuating device (if appropriate) is then carried out automatically by the system; thus, a working state is generated automatically. To this end, the detection means detect an insertion state defining a predetermined relative position between the pump unit and the pump actuating device (pump unit inserted or not inserted in pump actuating device) and transmit a corresponding signal to the control system (usually when the pump unit is inserted into the holding device). This signal actuates the drive device such that the attaching and coupling procedures are performed as soon as insertion is indicated. In this way, easy and safe operability of the medical pump is guaranteed. Uncoupling or detaching of the pump unit from the pump actuating device can also be detected so that the system is converted into a type of idle state.

In a working state the pump unit is connected to the pump actuating device such that an operating state is achieved, which makes the system (i.e. the medical pump) ready for use by the operator without this person having to perform any further steps. The working state exists when the pump unit is attached in the holding device and the pistons are coupled up in the coupling system. In an idle state the system has reached a state which allows the insertion of a new pump unit.

Preferably, at least one input element is provided, which is communicatively connected to an input of the control system and transmits a signal to the control system, whereby the control system for processing the signal is embodied such that a detaching and uncoupling position is taken up by the holding device and/or the coupling device.

As already noted above, the insertion state is detected and thereupon attaching and coupling procedures are carried out. A corresponding signal must be transmitted to the control system in order then to enable detachment and uncoupling of the pump unit or the pistons from the pump actuating device. This signal is generated by operation of the input element communicatively connected to the control system. In practice, the control system is embodied with a control panel or a touch screen, whereby appropriate pushbuttons or switches or even appropriate areas on a touch screen are provided, which enable indication of the desired severing of the connection between the pump unit and the pump actuating device. By appropriate actuation of an area on the touch screen (eject button), it is indicated to the control system that the pump unit should be removed from the pump actuating device. To this end, the drive device is actuated such that it drives the system into a detaching and uncoupling position. In this position, or no later than on reaching this position, uncoupling of the pistons and detachment from the holding device is carried out automatically by the system (the pump unit is then ready for removal in the pump actuating device). The operator may then carry out final removal of the pump unit from the pump actuating device.

In one disclosed embodiment, the detection means transmits a second detection signal, describing the non-presence of the pump unit in the pump actuating device, to the control system for controlling the drive device. The control system for processing the second detection signal controls the drive device to generate the idle state. Thus, final removal of the pump unit from the pump actuating unit is detected such that the pump actuating unit is converted into a state in which a new pump unit can be inserted into the pump actuating device. This state is basically the idle state.

Preferably, the detection means generates the detection signal and transmits it to the control system when the pump unit is inserted into the pump actuating device and/or is removed from it. Primarily, a signal (first detection signal) should then be generated and transmitted to the control system when the pump unit is inserted into the pump actuating device, or more precisely into the holding device. The operator may insert the pump unit into the holding device such that it is at least in a pre-latched state or is already completely attached therein. In any case, the detection means is "activated" by the insertion. In other words, the detection means detects the current state which is met by the relative position between the pump unit and the pump actuating device. Thus it is detected due to insertion that a pump unit is inserted in the holding device (conversely it can also be detected that no pump unit is inserted). The detection of this state and generation of the detection signal then initiates attaching and coupling. Complete attaching and coupling (if applicable) are carried out in a controlled manner by way of the drive, which is provided for actuating the pump itself. Separate drive devices are not necessary for this purpose. Moreover, detaching and uncoupling are also carried out by way of the drive.

Detection of the relative position between the pump unit and the pump actuating device enables precise and secure connection of the pump unit and pump actuating device at a predetermined time. The predetermined time is when the pump unit has been appropriately inserted into the holding device.

In one disclosed embodiment the detection means has a photoelectric barrier. An interrupter device for interrupting a light beam of the photoelectric barrier is provided on the pump unit. The photoelectric barrier supplies the first detection signal. In this manner, detection of the relative position and generation of the corresponding signal for actuating the drive is achieved in a simple manner. Preferably, the photoelectric barrier is a forked light barrier such that the interrupter device can be pushed into the fork in a simple manner. Forked light barriers are suitable for precise detection of the smallest objects and may be accommodated in the smallest installation space.

Preferably, the photoelectric barrier responds to reflection of the light emitted by a transmitter of the photoelectric barrier. This is particularly advantageous if the interrupter device is formed from a translucent material and therefore enables interruption of the light beam by means of the special development (e.g. by means of a bevel) in such a way that it reflects the light beam and thus a corresponding signal is triggered. The interrupter device may also be formed of an opaque material; thus triggering the photoelectric barrier by absorption.

Preferably, the photoelectric barrier works such that a "missing" signal at the receiver triggers the photoelectric barrier. Of course, it is also possible to provide a photoelectric barrier which has a transmitter and a receiver accommodated in separate housings or in which the transmitter and receiver are position adjacent to one another in one housing. In principle, any type of photoelectric barrier or similar sensor may be used here.

In one disclosed embodiment, the detection means has a pushbutton or switch device, whereby the pushbutton or switch device supplies the second detection signal. The pushbutton device is, for example, a microswitch or micro pushbutton. The pushbutton or switch is disposed in such a way on the holding device or on another component of the pump actuating device that it can be actuated without problem with insertion of the pump unit and, for example, remains in the actuated state as long as the pump unit is inserted. By operating the switch or pushbutton, the signal can be generated and transmitted to the control system as described above. However, it is also possible that the detection signal is generated only by releasing the pushbutton (also on renewed operation of a switch if applicable), i.e. removal of the pump unit from the pump actuating device is indicated. The control unit can then actuate the drive device in such a way that the pump actuating device is transferred into a predefined state, e.g. into the idle state, which enables the insertion of a new pump unit.

On using a pushbutton, this may remain actuated until the pump unit is removed form the pump actuating device. To this end, the pump unit preferably has an actuating device. It is also possible to provide a toggle switch, which is actuated during insertion and again during removal of the pump unit such that a corresponding signal is transmitted to the control system.

In this way, it is possible to detect the insertion state using only one detection means, namely both insertion of the pump unit and also the removal thereof. The first and second detection signals are thus supplied by the one detection means. It is, however, also further possible to provide separate detection means (at least two) for the first and second detection signal respectively such that, as described above, the photoelectric barrier supplies the first detection signal and the microswitch the second detection signal.

In one disclosed embodiment, the pump actuating device includes first snap-fit connection devices and the pump unit includes second snap-fit connection devices such that attaching or detaching of the pump unit to or from the pump actuating device and/or coupling or uncoupling of the pistons to or from the pump actuating device is effected by engagement of the first and second snap-in connection devices with each other or disengagement from each other. The pump unit is connected to the pump actuating device via two contact areas, namely the holding device and the coupling devices. Holding device and coupling devices are able to receive counterparts of the pump unit and can interlock securely. Only in this way is proper pump operation possible.

The first snap-in connection devices of the pump actuating device may be axle bolts of the holding device and retaining blocks and associated springs of the coupling devices, whilst the second snap-in connection devices of the pump unit may be retaining ribs on a valve cover and coupling noses on piston ends. As soon as the pump unit and the pump actuating device are joined together ready for operation, the axle bolts cooperate with the retaining ribs and the retaining blocks and associated springs cooperate with the coupling noses when the holding device and the coupling devices are closed. The axle bolts are disposed on the holding device in such a way that, when the pump unit is inserted into the holding device, they come into engagement both on the underside of the pump unit and also on the upper side, by means of one retaining rib on the valve cover in each case. Thus the axle bolts are in contact with the retaining ribs such that removal of the pump unit is no longer possible and the pump unit is securely in the grip of the holding device. The coupling noses of the pistons are embodied such that they are clamped between the spring ends of the springs in the retaining blocks and the pistons are thus clamped to be resistant to tension and shear. As a result, the pump unit is securely attached in the pump actuating device and the pump may be started up.

In another disclosed embodiment, the first snap-in connection devices may be claws on the holding device and retaining blocks and associated springs of the coupling devices. The second snap-in connection devices may be retaining noses on a cylinder head and coupling noses on the piston ends. The claws cooperate with the retaining noses and the retaining blocks and associated springs cooperate with the coupling noses when the holding device and the coupling devices are closed. Cooperation is provided similarly to the embodiment described above. However, in this embodiment there are claws disposed on the holding device which engage as hinged elements in the retaining noses on the pump unit. Thus, secure attachment of the pump unit to the pump actuating device is guaranteed.

The control system allows closing of the holding device and/or the coupling devices by automatic snapping in of the respective first and second snap-in connection devices performed by means of the drive device. The control system also allows opening of the holding device and/or the coupling device by automatic opening of the snap-in connection devices performed by means of the drive device. As described above, it should be possible to accomplish attachment, coupling, uncoupling and detachment automatically by appropriately controlling the drive device. By actuating the drive device and moving the retaining blocks by way of the drive device, it is possible to assign and actuate the snap-in connection devices to one another such that snapping in and opening thereof is performed automatically. High retention forces may be used since opening and closing is performed by the drive device.

The drive device may include a linear drive (or two linear drives in the case of two pistons) with spindle and motor for controllable driving of the spindles. It is possible by way of these linear drives to perform very precise movements with a low impact on the pump and its piston/cylinder units.

The two pistons or piston rods may be provided in cylinders and the pump actuating device allows for alternating displacement of the pistons. It is possible to ensure an increased pump delivery rate as a result. In this embodiment, the drive device may include two motors or a motor having controllable gears so as to be controllable in such a way that the pistons are operated in a manner deviating from alternating operation for the purpose of opening or closing of the holding device and/or the coupling devices. While in the normal pumping procedure the pistons are operated alternately, a different mode of operation with one and the same drive units is selected for opening or closing of the holding device and/or coupling devices which brings about simplified construction.

The motor control system or control system may be configured such that the pistons are displaceable at constant speed. The result of this is smoother delivery of the medium to be pumped.

The snap-in connection devices may be configured such that a force to be applied for closing is less than a force to be applied for opening, particularly in relation to the holding device. This is particularly advantageous in an embodiment where complete attachment is already provided for on inserting the pump unit into the holding device and only coupling of the pistons to the coupling system is performed automatically by actuating the drive device. The operator can then insert the pump unit effortlessly into the holding device. At the same time, a high retention force can be generated as it can easily be overcome by automatic opening.

The drive unit and the control system may be configured such that the snap-in connection devices fitted in the pump actuating device or the latching devices of the coupling devices are positioned such that, in an idle state prior to attaching of the pump unit and on connecting the pump unit to the pump actuating unit the latching devices are not engaged with the piston rods and the coupling devices are closable by actuating the drive devices. This means that the user need not undertake any major manipulations with respect to the pistons or piston positions in order to attach the pump unit to the pump actuating device. Here, as already described above, insertion of the pump unit into the holding device is detected and the drive device actuated in such a way that coupling takes place automatically.

BRIEF DESCRIPTION OF THE DRAWINGS

The disclosed embodiments will be described in more detail with reference to exemplary embodiments, which will be explained in greater detail with reference to the enclosed drawings.

FIG. 4 illustrates a lateral view of a holding device in the closed state.

FIG. 5 illustrates a holding device similar to that according to FIG. 4 but in a partial cross-section along the line V-V from FIG. 6.

FIG. 6 illustrates the arrangement according to FIG. 4 in a view from above.

FIG. 7 illustrates a lateral view of a holding device in the opened state.

FIG. 8 illustrates a holding device similar to that according to FIG. 7 but in a partial cross-section along the line VII-VII from FIG. 9.

FIG. 9 illustrates the arrangement according to FIG. 7 in a view from above.

FIG. 10 illustrates a perspective exploded view of functional units of the holding device.

FIG. 11 illustrates a perspective view of a sub-unit from FIG. 10.

FIG. 12 illustrates an exploded view of a sub-unit from FIG. 11.

FIG. 13 illustrates a perspective view of coupling devices.

FIG. 14 illustrates the coupling devices from FIG. 13 in a different slide position.

FIG. 15 illustrates an exploded view of a coupling device from FIG. 13 or 14.

FIG. 16 illustrates a perspective exploded view of a sub-unit of the arrangement according to FIG. 13.

FIG. 19 illustrates a view corresponding to that according to FIG. 17 but in a different operating state.

FIG. 20 illustrates a front view of the arrangement according to FIG. 19.

FIG. 21 illustrates a cross-section along the line XXI-XXI from FIG. 19.

DETAILED DESCRIPTION

Figure 1:
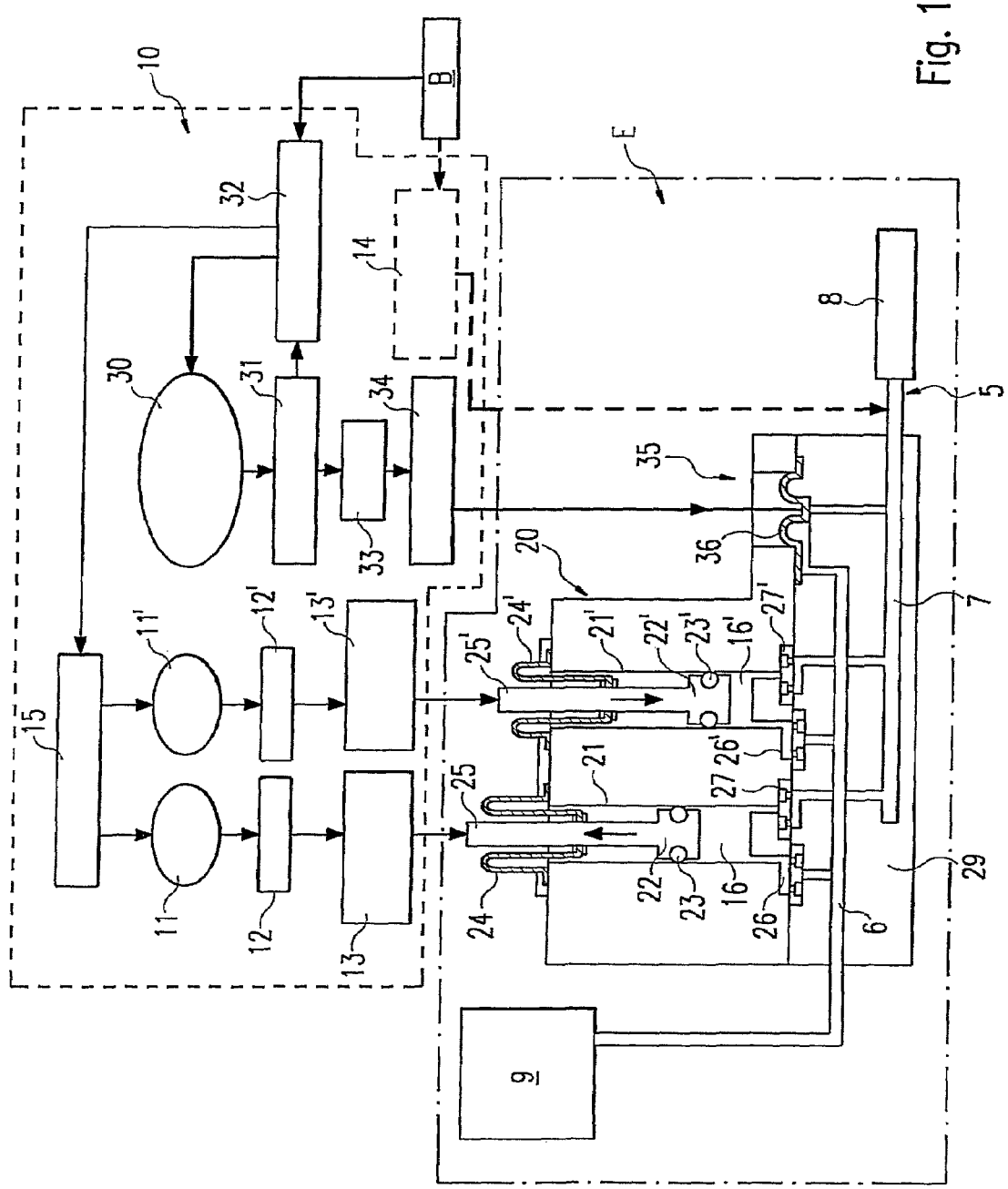
FIG. 1 illustrates a schematic block diagram of an embodiment of the medical pump.

The same reference numerals are used in the following description for identical parts and parts acting in an identical manner.

FIGS. 1 to 21 illustrate a first disclosed embodiment of the pump. FIGS. 22 to 44 illustrate a second disclosed embodiment that is modified in relation to the first embodiment. The detection means, as they have already been referred to above, are only shown and described with respect to the second embodiment (FIGS. 22 to 44). However, the detection means (or sensor devices) may also be provided in a pump system of the first embodiment (FIGS. 1 to 21); they are just not explicitly depicted. Further, FIG. 1 relates to both embodiments even though the reference numbers of only the first embodiment are included.

Referring to FIG. 1 a pump actuating device 10 is illustrated, which includes a motor control system 15 for controlling two motors 11, 11' that are linked by gears 12, 12' and coupling devices 13, 13' to piston rods 25, 25'. An operator B may, by means of appropriate switching devices (foot switch, finger switch), actuate motor control system 15 such that motors 11, 11' alternately displace piston rods 25, 25' by way of the chain described and thus pistons 22, 22' in cylinders 21, 21' of a pump unit 20 such that pressure chambers 16, 16' of pump unit 20 are alternately increased and decreased in volume.

Seals 23, 23' are provided on pistons 22, 22' to seal pressure chambers 16, 16' or pistons 22, 22' in relation to cylinders 21, 21'. Furthermore, piston rods 25, 25' are sealed so as to be germ-free by roll diaphragms 24, 24', which are permanently joined to cylinders 21, 21' and to piston rods 25, 25'. In this manner, germs from the ambient air, which without these roll diaphragms 24, 24' would settle on the inner walls of cylinders 21, 21' and which are allowed through by seals 23, 23', cannot mix with the working fluid or get into it.

In the second disclosed embodiment (FIGS. 22 to 44), bellows are provided instead of the roll diaphragms illustrated with respect to the first disclosed embodiment. In FIGS. 22 to 44, the seals (seals 23, 23') are not explicitly illustrated but are nevertheless necessary in order to define the pressure chambers as described above.

Referring again to FIG. 1, suction valves 26, 26' and pressure valves 27, 27' are connected to pressure chambers 16, 16'. Suction valves 26, 26' communicate with a reservoir 9 for the working fluid via a fluid inlet 6. Pressure valves 27, 27' communicate with a pressure hose 5 which leads to an applicator 8 via a fluid outlet 7. Pump unit 20, together with reservoir 9 and its contents, pressure hose 5 and applicator 8, form a disposable part E, which is disposed of after each operation so that the overall arrangement meets the highest possible sterility requirements.

The valves according to the second embodiment are not explicitly described as the principles correspond substantially to those according to the first embodiment, which are now described.

A clamp valve 14 (in addition to motor control system 15) allows for complete shut-off of the fluid flow to be effected by operator B.

Pressure regulating valve 35 allows a valve diaphragm 36 to open and close a connecting duct between fluid outlet 7 and fluid inlet 6. Diaphragm 36 is actuated by a push rod 34 and a spring 33 as well as a dynamometer 31 operated by a servomotor 30. Dynamometer 31 supplies a force-proportional output signal to a controller 32 by way of which an operator B may specify a maximum pressure. Instead of a separate dynamometer 31, it is also possible to measure the actuating current of servomotor 30 which is likewise force-proportional.

This arrangement ensures that the fluid pressure at applicator 8 can be precisely set. Moreover, pressure fluctuations arising due to actuation of the pistons are compensated for by control valve 35. Pressure control valve 35 is force-controlled rather than path-controlled due to its design, having a diaphragm on which the fluid pressure impinges. As a result, when coupling pump unit 20 to pump actuating device 10, no pressure adjustment error can arise even in the case of dimensional tolerances as it is not a matter of the geometrical dimensions (hence the path) but rather the force with which pressure control valve 35 is actuated.

The valve arrangement just described may also be used in conjunction with the second embodiment.

Figure 2:
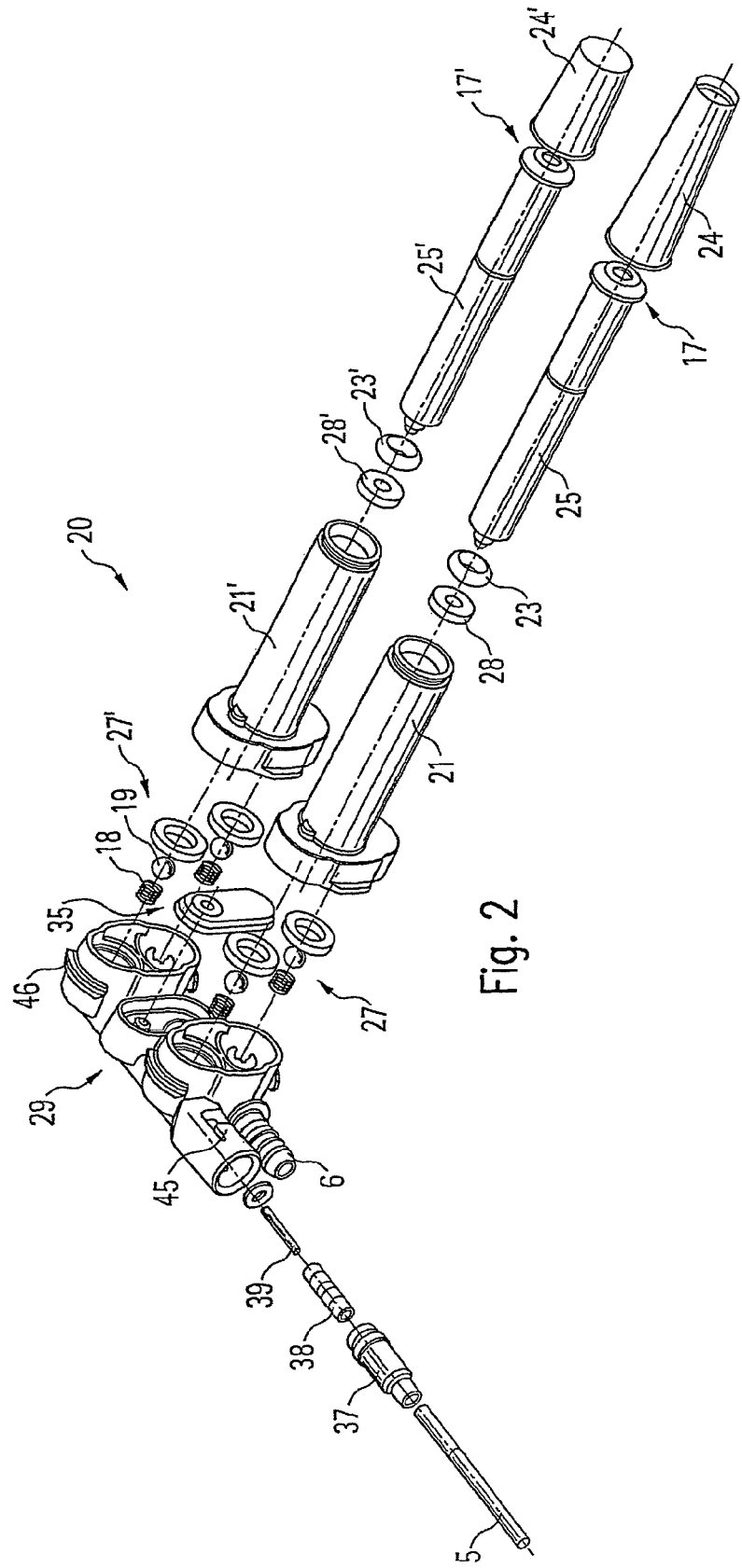
FIG. 2 illustrates a perspective exploded view of an embodiment of the pump unit.

FIG. 2 shows a structural embodiment of pump unit 20 in a perspective exploded view. Pressure and suction valves 26/27 include balls 19, which are pressed by way of springs 18 onto valve seats (not visible in the diagram) as is known to those skilled in the art.

Cylinder head 29 has two sections for coupling with cylinders 21, 21', whereby the valves sit between cylinders 21, 21' and cylinder head 29.

Furthermore, as can be seen from FIG. 2, piston rods 25, 25' have coupling noses 17, 17' at their distal ends byway of which a mechanical connection to coupling systems 13, 13' may be achieved.

The pistons are formed by proximal ends of piston rods 25, 25' having attached caps 28, which simultaneously hold seals 23, 23' firmly on piston rods 25, 25'.

Pressure hose 5 is irremovably attached to cylinder head 29 by way of an adapter sleeve 37, a crimp tube 38 and an inner tube to be inserted into pressure hose 5. After assembly (in any manner known to those skilled in the art) adapter tube 37 is held in cylinder head 29 by means of a spring tab 45 which irremovably holds adapter sleeve 37 in cylinder head 29.

Figure 3:
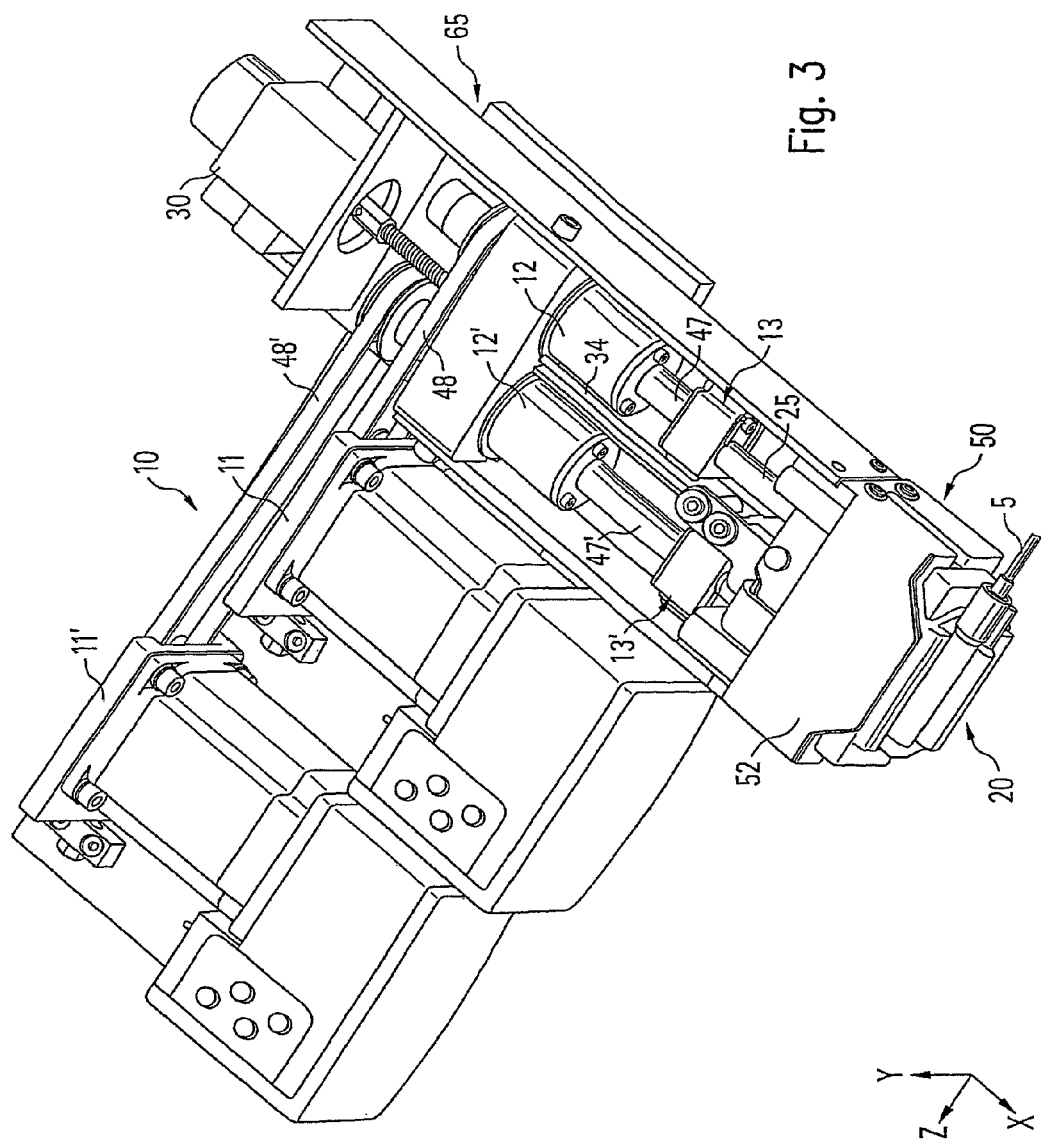
FIG. 3 illustrates a perspective view of the pump actuating device coupled with the pump unit.

FIG. 3 illustrates a perspective view of pump actuating device 10 coupled with pump unit 20. It is apparent from this diagram that the pump actuating device 10 has a frame 65 on which motors 11, 11' are attached. These are embodied as reversible motors, which drive spindles 47, 47' by way of toothed belts 48, 48' and gears 12, 12' such that the rotary motion of motors 11, 11' is converted into linear movements. Couplings 13, 13', to which piston rods 25, 25' are able to be coupled, are attached to spindles 47, 47'. The arrangement of servomotor 30 with its associated push rod 34 is also shown in FIG. 3.

Frame 65 is not explicitly shown in the embodiment of FIGS. 22 to 44 so that the components of the medical pump can be better illustrated. However, in this embodiment a frame or housing, which accommodates the essential components, is also provided.

Detection means are not explicitly illustrated in the embodiment of FIGS. 1 to 21 but are nevertheless provided in order to actuate the motors in such a way that a working state and an idle state can be generated. This operation will be explained in greater detail with respect to the embodiment of FIGS. 22 to 44. Explicit developments of the detection means will be described in greater detail with respect to the second embodiment.

Holding device 50 also attached to frame 65. Holding device 50 retains pump unit 20. Holding device 50 is now described in greater detail with respect to FIGS. 4-12.

Holding device 50 comprises claw retainers 52, 52' with claws 51, 51' on the end, which can engage with retaining noses 46 provided at pump unit 20 in order to hold pump unit 20.

Claw retainers 52, 52' (as illustrated in FIG. 4) are supported via rotary axes on frame 65 and preloaded by means of springs 53 (see FIG. 10) in the closed position (FIGS. 4-6). To insert a pump unit 20, the pump unit 20 is pressed into holding device 50 such that claws 51, 51' slide with front-side oblique surfaces over retaining noses 46 of pump unit 20 and are forced open. As soon as pump unit 20 is pressed in completely, claw retainers 52, 52' snap closed and claws 51, 51' hold pump unit 20 in this position until they are forced apart again.

The mechanism for opening holding device 50 or claws 51, 51' is now described in greater detail with respect to FIGS. 10-12.

Holding device 50 includes a retaining block 54 which has cylinder holders 56, 56' on its front side. Cylinder holders 56, 56' correspond to the rear sides of cylinders 21, 21' of pump unit 20. The fit is easily seen from a comparison of FIGS. 2 and 10.

An opening slide 57 is attached to retaining block 54 by fixing screws 59, 59' whereby holding slide 57 has slots 60, 60' such that it may be slid back and forth. Opening slide 57 is pushed backwards (away from pump unit 20) by means of a spring 58.

A rocker arm 62, bearing symmetrically disposed tabs 64, 64' is attached to opening slide 57 by a rocker arm bearing 63 so as to be pivotable back and forth. On its front end, which faces towards pump unit 20, opening slide 57 bears an opening tab 61. Opening tab 61 has a height corresponding to the distance between the inner surfaces of claw retainers 52, 52'. On these inner surfaces of claw retainers 52, 52' are attached opening ramps 55, 55' in the displacement path of opening tab 61 such that opening tab 61, on striking opening ramps 55, 55' and being further displaced towards pump unit 20, pushes apart claw retainers 52, 52' such that they move from the position illustrated in FIGS. 4-6 into the position illustrated in FIGS. 7-9. In this position (according to FIGS. 7-9), claws 51, 51' disengage from retaining noses 46 on pump unit 20 and thus release pump unit 20.

Displacement of opening slide 57 takes place as now described.

In the case of a "standard" actuation of pump unit 20, spindles 47, 47' are moved alternately back and forth such that in an end position of a spindle 47, 47' they take up the positions illustrated in FIG. 6 or 10. During these movements, retaining blocks 72, 72' of piston holders 70, 70' on the ends of spindles 47, 47' are moved past tabs 64, 64' such that rocker arm 62 is either tilted in a counter-clockwise direction, as illustrated in FIG. 6 or 10, or in the other direction in which retaining blocks 72, 72' are in the reversed position—pushed forward and pulled back. These alternating movements of piston holders 70, 70' and retaining blocks 72, 72' may be carried out to actuate the pump without displacing opening slide 57 towards pump unit 20.

However, when spindles 47, 47' are driven in such a way that both piston holder 70, 70' and retaining blocks 72, 72' are running side by side, rocker arm 62 cannot move out of the way on being pushed forward (towards pump unit 20) with the result that both retaining blocks 72, 72' engage simultaneously with both retaining tabs 64, 64'. As a result of this engagement, on a further forward movement of piston holders 70, 70', opening slide 57 is displaced in its slots 60, 60' against the force of spring 58 towards pump unit 20, such that opening tab 61 slides over opening ramps 55, 55' and thus forces claw retainers 52, 52' apart. As a result, the engagement of claws 51, 51' in relation to retaining noses 46 on pump unit 20 is released. This opening of holding device 50 is thus effected exclusively by motor control system 15 via motors 11, 11' and their corresponding control system.

The action or actuation of coupling systems 13, 13', with which piston rods 25, 25' are coupled by way of their coupling noses 17, 17' to piston holders 70, 70', will now be described in greater detail. Reference is made to FIGS. 13-21.

Retaining blocks 72, 72' are screwed onto spindles 47, 47' in accordance with FIG. 15 and have insertion openings 77, 77' into which piston rods 25, 25' may be inserted with their coupling noses 17, 17'. Springs 71, 71' are attached to retaining blocks 72, 72' in such a way that spring ends 73, 73' protrude into insertion openings 77, 77'. The spacing of spring ends 73, 73' is such that piston rods 25, 25' may be inserted into insertion openings 77, 77' with their coupling noses 17, 17' and in the process force spring ends 73, 73' apart until they snap together behind coupling noses 17, 17'. Coupling noses 17, 17' are tapered at their ends for this purpose. After insertion of coupling noses 17, 17' into piston holders 70, 70', piston rods 25, 25' are firmly connected (resistant to pulling and pushing) to piston holders 70, 70'.

Between the displacement paths of piston holders 70, 70' and retaining blocks 72, 72' respectively, a split lever 74 is pivotably attached to a pivot bearing 75. The split lever 74 has on its upper and lower surface (e.g., on the side facing away from pump unit 20) expansion surfaces 76, 76'. On the other end (e.g. the side facing towards pump unit 20) pivot edges 78, 78' are provided on split lever 74.

Figure 17:
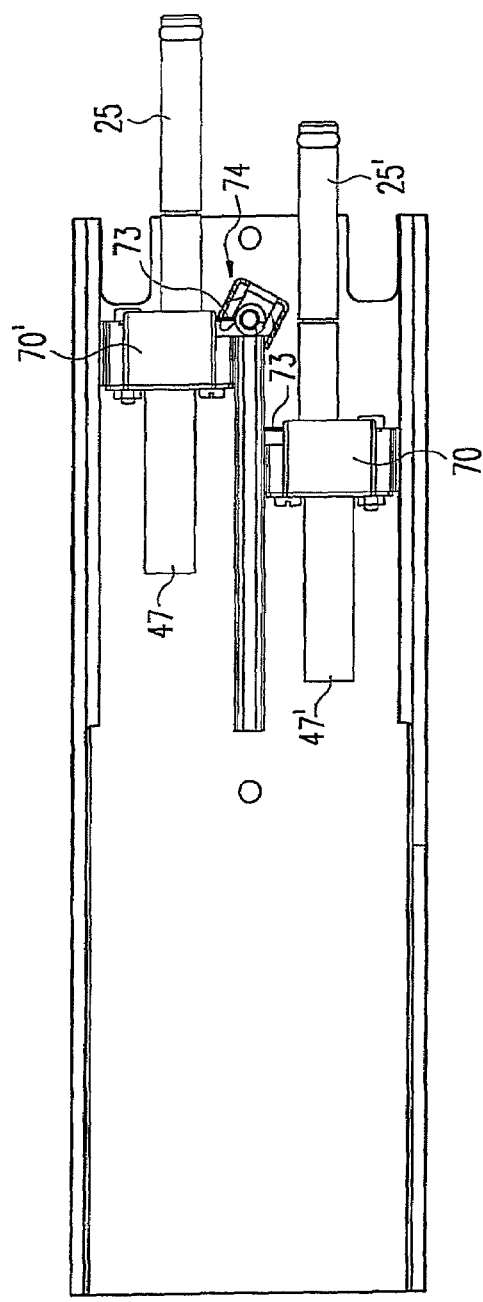
FIG. 17 illustrates a view from above of the arrangement according to FIG. 13 coupled with piston rods.
Figure 18:
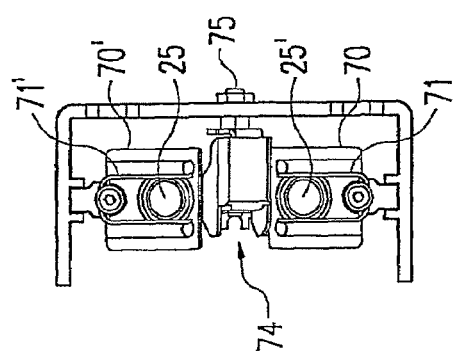
FIG. 18 illustrates a front view of the arrangement according to FIG. 17.

The arrangement and dimensioning of split lever 74 with its expansion surfaces 76, 76' and pivot edges 78, 78' is selected such that with an alternating movement of retaining blocks 72, 72' and piston holders 70, 70', as is illustrated in FIGS. 13 and 17, split lever 74 is tilted towards either one side or the other, depending on which of piston holder 70, 70' and retaining blocks 72, 72' slides past it on its path towards pump unit 20. Due to this pivoting, expansion surfaces 76, 76' are pivoted in such a way that they cannot engage with spring ends 73, 73' of respective piston holder 70, 70' which are sliding past. However, when both piston holders 70, 70' and retaining blocks 72, 72' are displaced in parallel side by side towards pump unit 20 (see FIGS. 14 and 19-21), expansion surfaces 76 and 76' engage with spring ends 73, 73' (see particularly FIGS. 20 and 21) such that they slide along (inclined) expansion surfaces 76 and 76' respectively and are forced apart. As a result of this forcing apart, the piston rods 25, 25' that were previously held tight at their coupling noses 17, 17' (see stop position according to FIG. 18), are released as is illustrated in FIG. 20. Once holding device 50 has been opened and claws 51, 51' have been forced apart and thus their engagement with retaining noses 46 of pump unit 20 has been released (by means of the same simultaneous and parallel movement of piston holders 70, 70' and retaining blocks 72, 72') then on parallel displacement of piston holders 70, 70' up to their forward position facing pump unit 20, the user can remove the pump unit without applying force.

Furthermore, motor control system 15 is configured such that after removal of pump unit 20 from pump actuating device 10, both spindles 47, 47' retract piston holders 70, 70'. Thus, if the user inserts a pump unit 20 into pump actuating device 10, then he only needs to overcome the force necessary for opening holding device 50. Piston rods 25, 25' then protrude with their coupling noses 17, 17' through cylinder holders 56, 56' into pump actuating device 10. The user can then actuate motor control system 15 to move piston holders 70, 70' towards pump unit 20 in a "coupling mode" until coupling noses 17 and 17' respectively push apart spring ends 73, 73' and snap into place. This process of snapping into place is carried out separately for both coupling noses 17 and 17' one after the other such that split lever 74 does not open springs 71, 71'.

In this case, therefore, insertion of pump unit 20 into holding device 50 is detected. A detection signal D, D' generated due to this detection (pump unit 20 is located in the holding device 50) causes the control system to actuate the motors 11, 11' in such a way that the coupling mode can be carried out automatically, i.e. coupling of the pistons in the pump actuating device 10 and thus the creation of a working condition is carried out automatically. The detection means may be embodied, for example, as a photoelectric light barrier. Details of the detection means will be described in greater detail with respect to the second embodiment.

The second embodiment will now be described, referring to FIGS. 22 to 44. Insertion and removal of the pumps unit or pump unit into or from the pump actuating device is carried out essentially according to the principles already described on the basis of the embodiment according to FIGS. 2 to 21 and thus will not be described in detail with respect to the second embodiment. Different developments of individual components of the second embodiment and any variation in the mode of functioning will, however, be described in detail. Thus, for example, in the second embodiment, detection means or sensor devices are illustrated which make it even easier for the user to operate the medical pump. It must be pointed out, however, that the detection means may also be provided with the medical pump according to the first embodiment.

The arrangement of the valves and their function in conjunction with reservoir, applicator and hose connections (e.g. pressure hose) will not be explicitly described in the second embodiment. In this case, the first embodiment should be referred to. The same applies to regulation of the fluid flow and the pressure. Additionally, the reservoir and applicator will not be illustrated explicitly with respect to the second embodiment. Reference is made in this case, for example, to FIG. 1.

Figure 22:
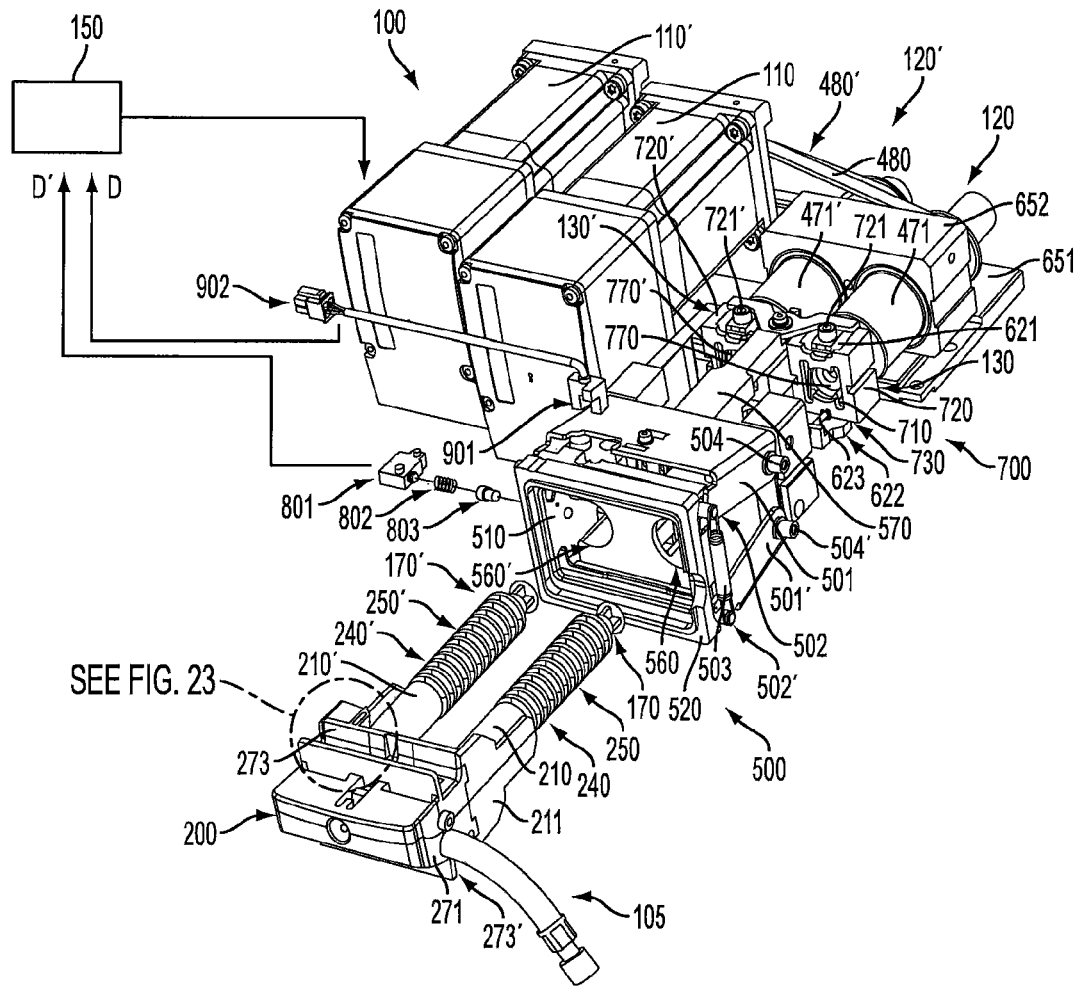
FIG. 22 illustrates a perspective view of the pump actuating device with not yet coupled with a pump unit, according to an additional embodiment.

FIG. 22 illustrates a perspective view of pump actuating device 100 with pump unit 200 not yet coupled up. Further details of pump actuating device 100 and pump unit 200 are explained with reference to FIG. 22.

Pump actuating device 100 has motors 110, 110', which drive spindles (not visible here) by way of toothed belts 480, 480' and gears 120, 120' such that the rotary motion of motors 110, 110' is converted into linear movements and thus piston motion is achieved. Motors 110, 110' and gears 120, 120' form drive devices. The motors 110, 110' are controlled via a control device or control system 150. The spindles are inserted in spindle holders 471, 471', which are supported by way of a bearing pedestal 652. Bearing pedestal 652 is disposed on a base plate 651, which also accommodates motors 110, 110'. Also disposed on the base plate 651 is a frame (not illustrated in FIGS. 22 to 44) which accommodates the spindle holders 471, 471'. The spindles are attached to coupling devices 130, 130', whereby the coupling system has retaining blocks 720, 720' of a piston holder 700. The piston holders 471, 471' can be moved with the retaining blocks 720, 720' due to movement of the spindles by way of the motors 110, 110'.

Pump actuating device 100 also has a holding device 500 which is provided for retaining pump unit 200. Holding device 500 includes a retaining device 510 with a retaining frame 520. Holding device 500 also includes cylinder holders 560, 560', as described with respect to the first embodiment. Provided in retaining frame 520 are axle bolts 502, 502' running crosswise within the frame 520 each disposed on a top and bottom side of the frame 520, said bolts 502, 502' protruding with their ends over the frame 520 on its side areas. The axle bolts 502, 502' are inserted in grooves of the frame 520 and may be countersunk. The opposing ends of axle bolts 502, 502' each on a lateral surface of frame 520 protrude from the frame 520 via cut-outs and are joined together with tension springs 503, 503'. In addition, holding device 500 is embodied with clutch release levers 501, 501', which may be opened and closed as hinges by way of cylindrical pins 504, 504' supported on retaining device 510 and which overlap retaining device 510 in each case on its top and bottom side (the cylindrical pins 504, 504' are supported, for example, by way of plain bearings). Thus the clutch release levers 501, 501' enclose the receiving device in the shape of jaws. Axle bolts 502, 502' are supported on their respective ends on arms of the clutch release levers 501, 501' and are moved towards or away from each other by way of the clutch release levers (in the manner of jaws, e.g., pulled out of the grooves or pushed back into them).

As can also be seen in FIG. 22, a photoelectric barrier, in this case a forked light barrier 901, is disposed on the top side of holding device 500, the barrier 901 protruding into the interior of holding device 500. Photoelectric light barrier 901 is connectable by way of a plug element 902 to control system 150, which is also responsible for controlling the motor 110, 110'. A microswitch 801 is provided on a side wall of retaining device 510, such that actuating pin 803 of microswitch 801 protrudes into the interior of holding device 500. Microswitch 801 is connected to control system 150. Actuating pin 803 is operable by way of a compression spring 802 and provides control system 150 with a corresponding signal based on actuation or non-actuation. Both detection means (photoelectric light barrier 901 and microswitch 801) transmit a generated signal (first and second detection signals D, D') to control system 150 such that it activates the motors 110, 110' based on the signals D, D'. The motors 110, 110' eventually enable the travelling motion of the piston holders 700, 700' and retaining blocks 720, 720' and alignment of the holding device 500 in order to enable connecting and also releasing of pump unit 200 and pump actuating device 100. Details of this are now described in greater detail.

Pump unit 200 has a cylinder block 211, in which cylinders 210, 210' are disposed and which is formed integrally with a valve cover 271 (the valve cover 271 encloses the suction 26, 26' and pressure valves 27, 27' described with FIG. 1). Pistons 250, 250' (not visible here) are each connected to a bellows 240, 240' (whereby each bellows 240, 240' is also connected to one of the cylinders 210, 210') and thus are covered outside the cylinders 210, 120' by means of the bellows 240, 240'. The respective ends of the pistons 250, 250' have coupling noses 170, 170' by way of which the pistons can be accommodated on coupling devices 130, 130' of pump actuating device 100. A (first) retaining rib 273, 273' is formed on the bottom and top side of valve cover 271, running crosswise over the valve cover 271 (transverse to the alignment of the cylinders 210, 210'). A second rib (not shown) arranged parallel to the first may also be provided on the valve cover 271. Retaining ribs 273, 273' (which in relation to the respective second ribs are disposed nearer in the direction of the pistons 250, 250' or cylinders 210, 210') are configured such that axle bolts 502, 502' come to rest behind them (and thus between the two ribs), when pump unit 200 is accommodated in holding device 500. An additional rib on the top side of valve cover 271 is disposed on retaining rib 273, 273', perpendicular to the retaining rib and perpendicular to the upper side of the valve cover 271. The additional ribs acts as an interrupter device 272 for interrupting, e.g. reflecting, a light beam of forked light barrier 901 as soon as pump unit 200 is inserted in pump actuating device 100. The exact method of functioning is explained in greater detail further on.

Figure 23:
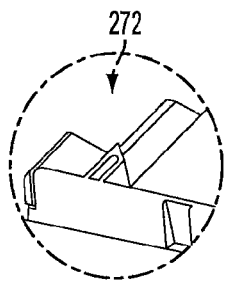
FIG. 23 illustrates an enlarged detail view from FIG. 22.

FIG. 23 illustrates interrupter device 272 or the interrupter lug in an enlarged view.

As already described above, detection means are provided that detect an insertion condition (pump unit 200 inserted or not in pump actuating device 100), whereupon the control system activates the motors 110, 110' such a way that they move the piston holders 700, 700' correspondingly byway of the spindles 470, 470', particularly for attaching the pump unit 200 in the holding device 500 and coupling the pistons 250, 250' to the coupling system. However, uncoupling and detachment are also performed automatically by the system. In this case, the system (i.e., the piston holders 700, 700') runs through corresponding positions which should be described briefly. When a "moving of the retaining blocks" is referred to in the following, this means that the motors 110, 110' move the spindles and in the process they take with them the coupling devices 130, 130' (i.e., the piston holders 700, 700' and thus the retaining blocks 720, 720'). At the same time (or at least close in time) the holding device 500 is also correspondingly aligned in the relevant position in order to facilitate attaching or detaching of the pump actuating device 100. The corresponding positions thus define in each case the position of the retaining blocks 720, 720' and thus the coupling devices 130, 130' and also the alignment of the holding device 500. Thus the holding device 500 and the coupling devices 130, 130' take up the relevant position.

Figure 37:
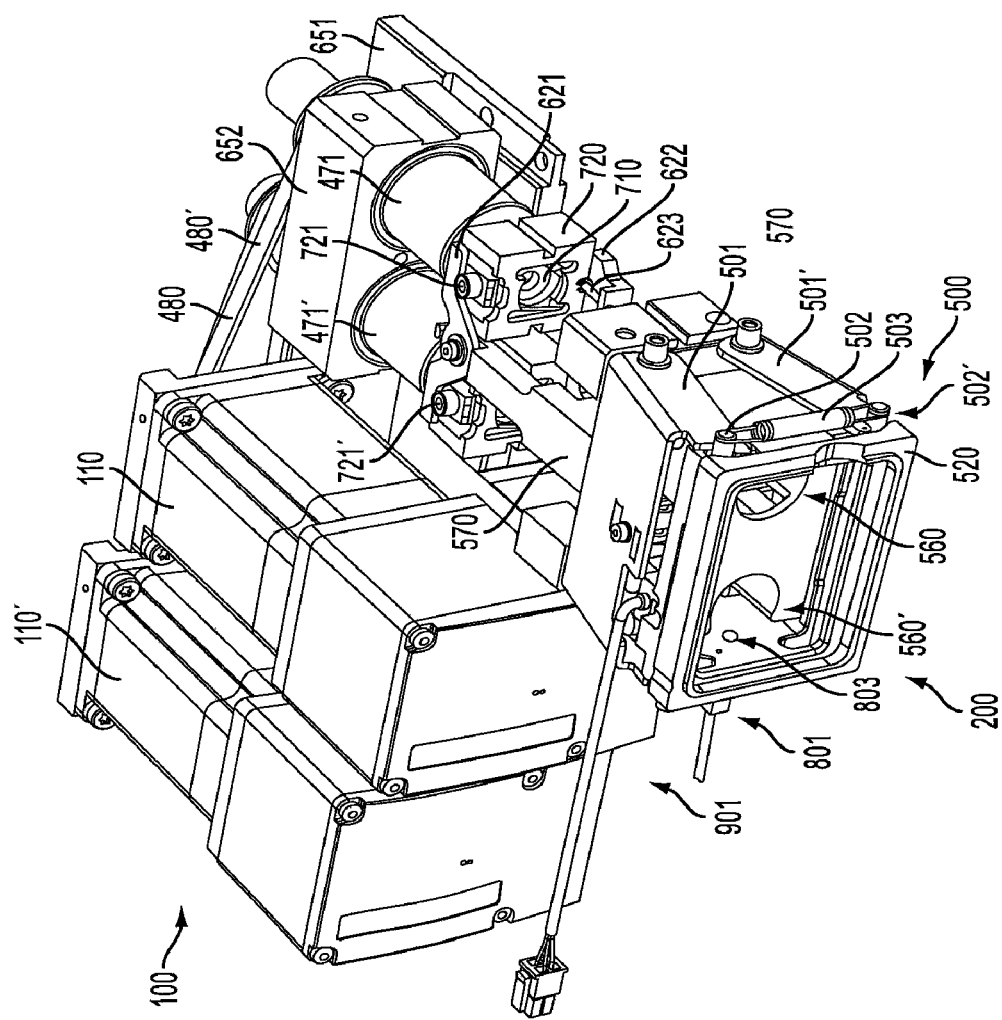
FIG. 37 illustrates a perspective view of the pump actuating device.

To start up pump actuating device 100 (e.g., switching on of the pump 200) it must be switched on. This may be performed, for example, by means of a switch or an appropriate area on a touch screen or similar input element. Following activation, the stepping motors 110, 110' must be aligned with respect to their positioning. To this end, a reference run is carried out and the retaining blocks 720, 720' are moved to a reference position. This means that the retaining blocks 720, 720' are moved backwards such that they are essentially in contact with the spindle holders 471, 471' (FIG. 37).

Subsequently, the retaining blocks 720, 720' are moved into an insertion position. In this position, which lies in front of the reference point when looked at from the holding device 500 in the direction of the spindle holder 471, 471', the axle bolts 502, 502' are already drawn slightly out of the grooves on the top and bottom side of the frame (because the clutch release levers close easily and are pulled together by the tension springs). The axle bolts 502, 502' are thus drawn into the open space inside the frame (e.g. FIG. 22).

An operator B can now insert the pump unit 200. The cylinder block 211 is configured such that it pushes the axle bolts 502, 502' apart again slightly using lateral surfaces appropriately bevelled for "threading", thus pushing them back again briefly into the grooves such that retaining ribs 273, 273' can be pushed via the grooves into the retaining frame 520. As soon as the retaining ribs 273, 273' are located in the retaining frame 520 and the lateral surfaces of the cylinder block 211 release the axle bolts 502, 502' again (simply because the lateral surfaces disposed on the retaining ribs close with the ribs), axle bolts 502, 502' (finally behind retaining ribs 273, 273') are pulled out of the grooves again due to the force of the tension springs and positioned behind the retaining ribs 273, 273' (between the two respective ribs). The pump unit 200 is then in a pre-latched condition and can no longer be pushed out of the holding device during coupling of the pistons 250, 250'. This means that the axle bolts 502, 502' are disposed behind the retaining ribs 273, 273' such that removal of pump unit 200 is prevented by the interaction of retaining rib 273, 273' and axle bolt 502, 502'.

Insertion of the pump unit 200 is detected by the detection means (described above) such that the retaining blocks 720, 720' are moved into a attaching and coupling position due to the first detection signal D thus generated or provided by the detection means. This position in turn is ahead of the insertion position whereby the retaining blocks 720, 720' are substantially in contact with the holding device 500. In this position, the pistons 250, 250' of the pump unit 200 (as described below in greater detail) are coupled to the coupling system or the retaining blocks 720, 720'. Essentially simultaneously (or, if need be, slightly staggered in time), the clutch release levers 501, 501' are closed completely by the forward travelling movement such that the pump unit 200 is securely attached in the holding device 500. The medical pump is then ready for operation (pump operation e.g. FIG. 29).

The retaining blocks 720, 720' are moved into a standby position which is located between the insertion position and the attaching and coupling position. The attaching and coupling routine is ended or ends when the retaining blocks 720, 720' with the pistons 250, 250' have been moved by the control system (software control system) into this predefined standby position appropriate for pump operation. From this position, the operator can initiate actual pump operation by activating a manual switch, foot switch or similar switch or pushbutton.

Ending of pump operation is indicated by releasing the foot switch or manual switch (also finger switch or similar switching element). Pump operation is thus carried out as long as the foot switch or manual switch is depressed. Basically, it would also be possible to indicate the desired ending of pump operation by a repeated actuation of the relevant switch. The operator can then decide whether he wants to continue with pump operation (repeated actuation of the manual or foot switch) or whether the pump unit 200 should be removed from the pump actuating device 100.

As the pump unit 200 and possibly also the supply hose from the fluid reservoir 9 (separating medium) to the pump unit 200 are not yet filled with fluid after insertion (but prior to starting up) of the same into the holding device 500 and thus immediate use of the medical pump is not guaranteed, an automatic filling and aspiration process could follow after the attaching and coupling process. This would have the advantage that the time until the fluid is actually available at the applicator 8 on initial activation could be shortened significantly. The minimum requirements for efficiency of the prefill routine are as follows: The supply hose must be correctly connected to the pump unit 200 and to the reservoir 9 and there must be enough separating medium in the reservoir.

If removal of the pump unit 200 is to be performed, the desired removal must be indicated to the control system 15. This is effected, for example, by actuation of an appropriate button, switch (e.g. eject button) or similar input element. In practice, this may also be performed by touching an area appropriately provided for the purpose on a touch screen. The motors 110, 110' are correspondingly activated by the control system 15 such that the retaining blocks 720, 720', due to the indication that the pump unit 200 should be removed, are driven completely backwards again until they are substantially in contact with the spindle holders 471, 471'. In this position, a detaching and uncoupling position (which from the point of view of positioning corresponds to the reference position), the pistons 250, 250' are thrown out of the retaining blocks 720, 720' again (e.g., uncoupled). Immediately after uncoupling, the clutch release levers 501, 501' are completely open again such that the pump actuating device 100 can be removed again by the operator (e.g., FIG. 34 or 36).

Removal of the pump unit 200 is also detected again. The retaining blocks 720, 720' are moved into the insertion position due to the removal detected. In this position, a pump unit 200 can be inserted again. In order to prevent repeated, unintentional attaching and coupling of the pump unit 200 already used, this procedure (that is to say moving into the insertion position) is preferably carried out with a time delay. In this case, the time is allocated in such a way that the user can remove the pump unit 200 effortlessly in the detaching and uncoupling position but insertion of a new pump unit can also take place without any noticeable delay. Travelling into the insertion position corresponds to generation of the idle state.

The insertion of pump unit 200 into pump actuating device 100, attaching of the pump unit in holding device 500 and coupling of pistons 250, 250' to coupling system 130, 130' will be described subsequently on the basis of FIGS. 22 to 28.

The pump system is started up (switched on). One after the other, controlled by control system 150, the reference and insertion positions are approached (retaining blocks 720, 720' are moved correspondingly). The insertion position is illustrated in FIGS. 22 to 28. The insertion position enables pre-latching of pump unit 200 to be inserted later, as described above.

An operator B then pushes pump unit 200 into holding device 500 by way of cylinder holders 560, 560'. Clutch release levers 501, 501' are still open in this position.

When the operator inserts the pump 200 properly, a light beam of photoelectric barrier 901 is interrupted (and in this case reflected) because interrupter device 272 (or interrupter tab) is introduced between the forks of the photoelectric barrier 901. The photoelectric barrier 901 is configured such that is responds to interruption of the light beam. Normally, the pump unit 200 is defined as a sterile product and designed, for example, as an injection-moulded plastic part. The material of the housing sections of the pump unit 200 may, for example, be made from a special polycarbonate capable of sterilisation by gamma rays. This material is translucent and is not capable of interrupting the light beam of the photoelectric barrier 901. Therefore, interrupter unit 272 (as a component of the injection-moulded plastic part) is designed such that the part which dips into the photoelectric barrier 901 brings about a reflection of the light emitted by a transmitter of the photoelectric barrier 901 and "triggers" the photoelectric barrier 901, (e.g., a forked light barrier). The interrupter device has, for example, a corresponding bevel on which the light beam is reflected, if need be is even totally reflected. This means the reflection may also be a total reflection. In this embodiment, the light beam would hit the interrupter device, penetrate it and be reflected on the bevel. This means that a signal, first detection signal D, is generated due to interruption of the light beam or is provided by the photoelectric barrier 901, whereby the signal D is then transmitted to control system 150. This causes the motors 110, 110' to set piston holders 700, 700' in motion again by way of spindles 470, 470' and to approach the attaching and coupling position.

Microswitch 801 is actuated simultaneously with insertion of pump unit 200 into holding device 500. Actuation is effected via a side wall of cylinder block 211, whereby the lateral wall ultimately presses actuating pin 803 of microswitch 801, (e.g., actuates it), due to insertion of the pump unit 200. The cylinder block 211 has, as previously described, the bevelled lateral surfaces which are chamfered on an end pointing towards the pistons 250, 250' and spindle holders 471, 471'. As a result, the side walls of the cylinder block 211 (in particular one side wall) can easily be guided over the actuating pin 803 of the microswitch 801 in order to activate it. By activating the microswitch 801, motor control system 150 indicates that a pump unit 200 is inserted. The more precise significance of the microswitch 801 will be described in even greater detail further on.

Figure 42:
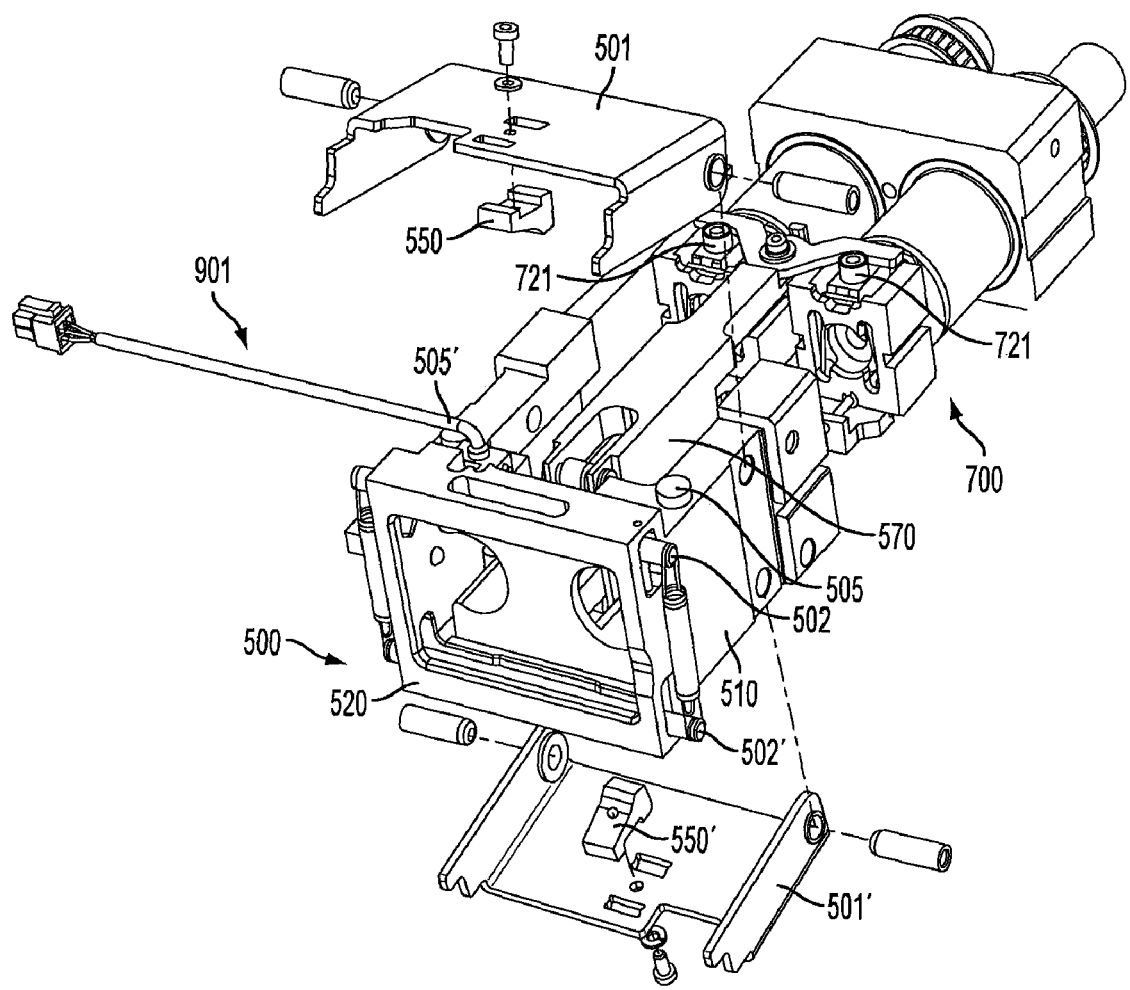
FIG. 42 illustrates an exploded view of an opened holding device.

In the following, activation of clutch release levers 501, 501' by moving retaining blocks 720, 720' will be described, i.e. their opening and shutting in the manner of jaws (particular reference in this case is made to FIGS. 42 and 43). Driving of the piston holders 700, 700' takes place—as already described above—due to the signal generated by the interrupted photoelectric barrier 901 and transmitted to the control system 150.

Attached to holding device 500 byway of a guide 571 for the opening slide is an opening slide 570, whereby guide 571 has slots such that the opening slide 570 may be slid back and forth in the guide 571. Attached to opening slide 570 is a rocker 621, which is additionally supported byway of both retaining blocks 720, 720'. At the same time, supporting devices (screw elements in this case) 721, 721' are disposed on a top side of retaining blocks 720, 720', which carry rocker 621 and therefore opening slide 570, among other things, in the relevant direction when both rocker arms are engaged with the supporting devices 721, 721' and the piston holders 700, 700' do not move consistently asynchronously relative to each other, that is to say not consistently at essentially the same speed. For example, if both piston holders 700, 700' move synchronously or substantially in parallel in the same direction (or at least such that no consistently alternating pump operation would be possible) towards holding device 500, that is to say into the attaching and coupling position, then opening slide 570, guided in guide 571, is likewise moved towards holding device 500. Of course, this also applies to the opposite direction. In pump operation with essentially asynchronous movement of the piston holders 700, 700', the rocker 621 and therefore the opening slide 570 are not displaced, as the opening slide 570 should be left in the position which enables operation of the pump 200.

Figure 39:
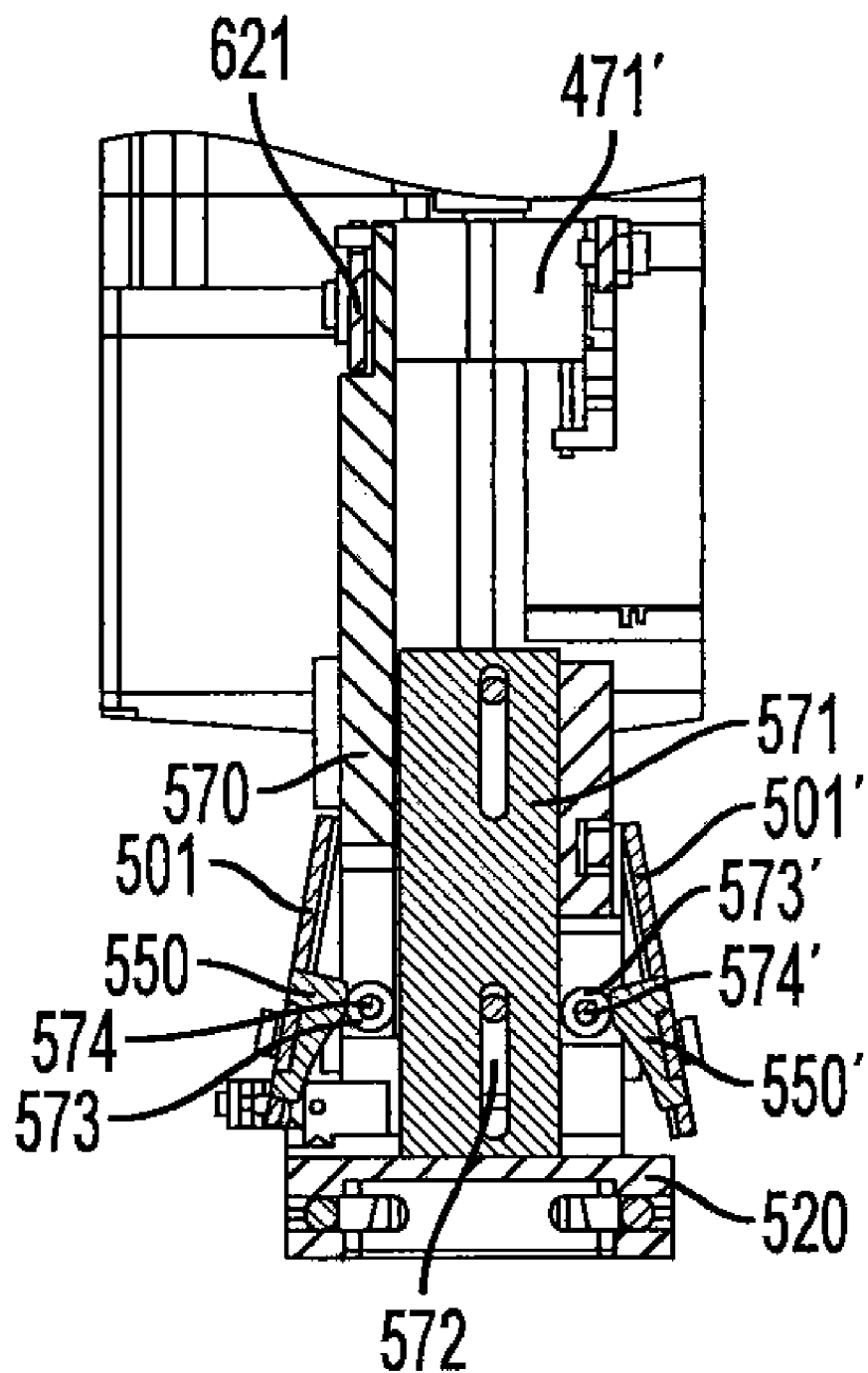
FIG. 39 illustrates a cross-section along the line XXXIX-XXXIX from FIG. 38.
Figure 43:
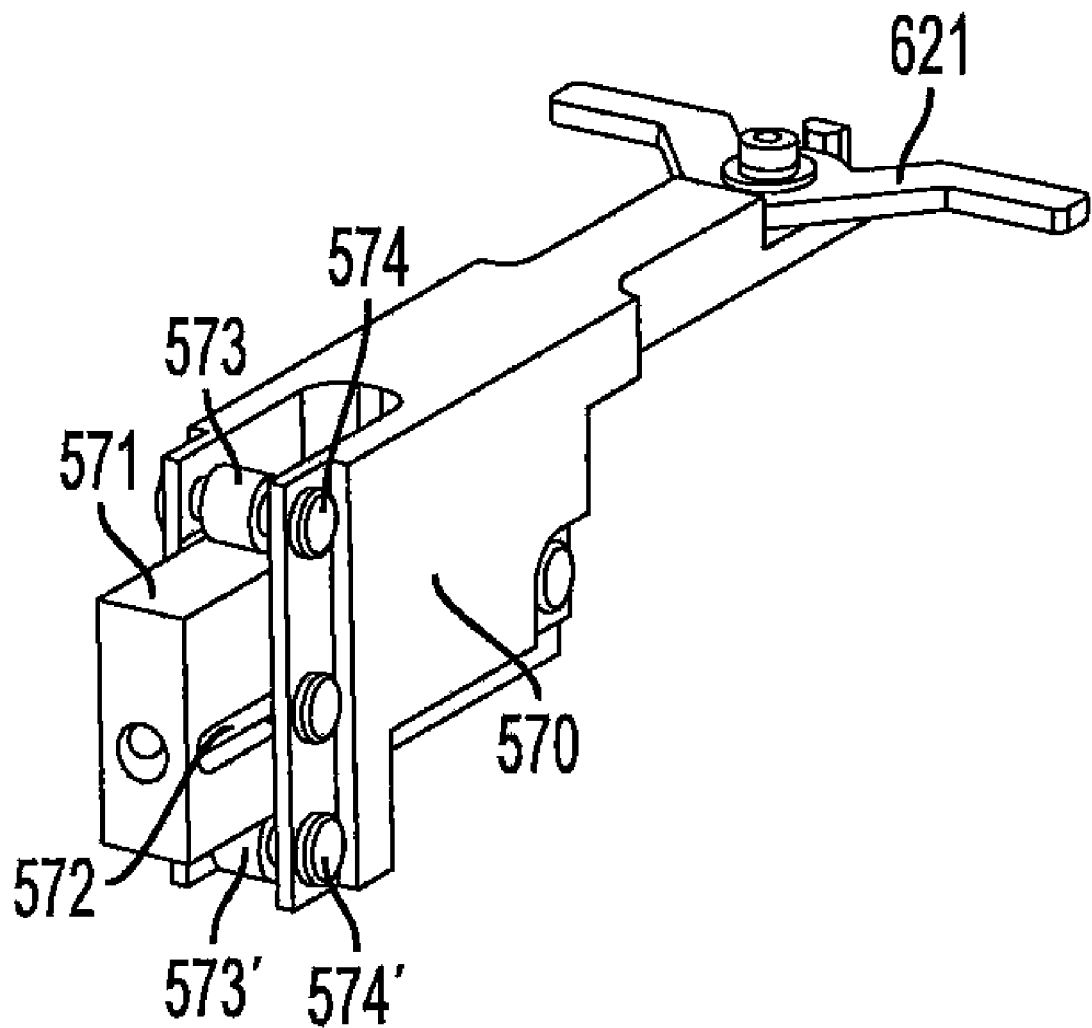
FIG. 43 illustrates a perspective view of an opening slide.

Opening slide 570 is illustrated in detail in FIG. 43. The opening slide 570 is guided in the guide 571 byway of slots 572. Furthermore, disposed on the slide 570 are an upper and a lower plain bearing 573, 573' supported by way of axle bolts 574, 574'. Plain bearings 573, 573' of the opening slide glide 571 along inner surfaces of the clutch release levers 501, 501', whereby opening ramps 550, 550' are provided on the inner surfaces in their displacement path. Due to the travelling movement of opening slide 570 along guide 571 by way of slots 572, the plain bearings 573, 573' move clutch release levers 501, 501 apart or together again on striking the opening ramps 550, 550' and on further displacement of opening slide 570 such that it is possible to perform complete opening and closing of clutch release levers 501, 501'. Opening of the clutch release levers 501, 501' is achieved by retracting the piston holders 700, 701' and therefore the rocker 621 with the opening slide 570 in the direction of the reference position. Conversely, closing is achieved by the opposite movement. On opening clutch release levers 501, 501', tension springs 503, 503' are stretched and hold the clutch release levers 501, 501' together. As illustrated in FIG. 39, the plain bearings 573, 573' are each at the highest possible level of the opening ramps 550, 550' when the opening slide is completely retracted and the clutch release levers are fully open. Clutch release levers 501, 501' are supported on elastically deformable elements disposed on the retaining device, preferably rubber elements 505, 505' to prevent them from rattling.

Figure 25:
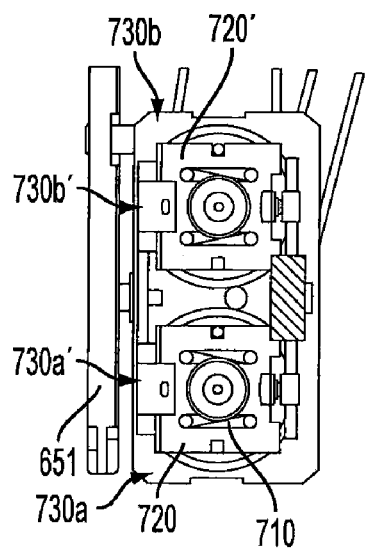
FIG. 25 illustrates a cross-section along the line XXV-XXV from FIG. 24.
Figure 26:
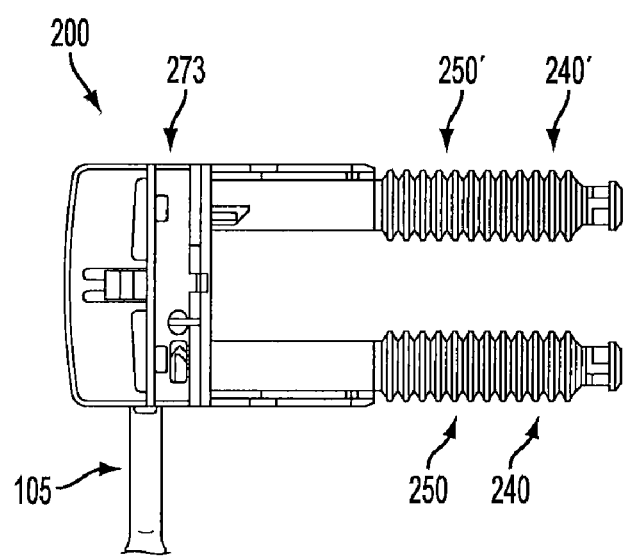
FIG. 26 illustrates a view from above of the pump unit according to FIG. 22.
Figure 27:
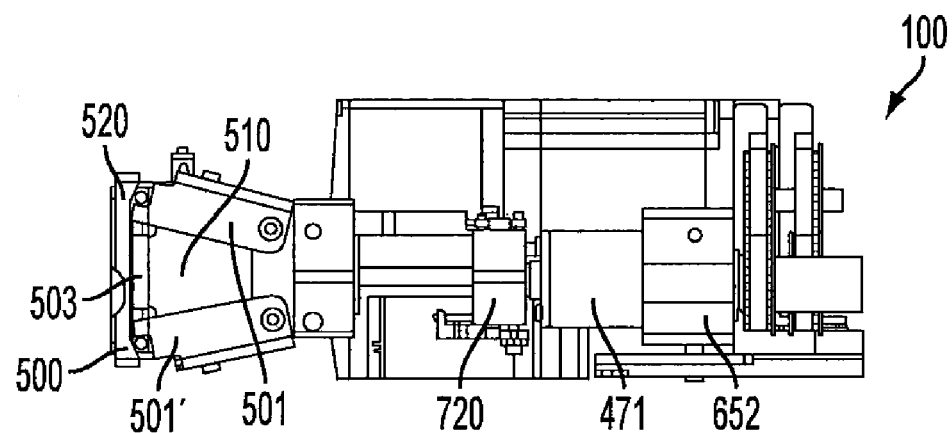
FIG. 27 illustrates a lateral view of the pump actuating device according to FIG. 22.
Figure 28:
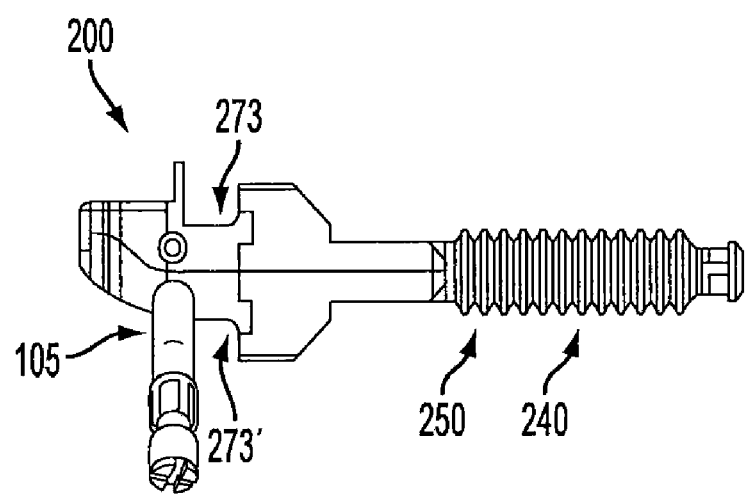
FIG. 28 illustrates a lateral view of the pump unit according to FIG. 22.

FIGS. 24 and 26 to 28 illustrate the perspective view according to FIG. 22 in views from above and lateral views. It can particularly be seen from FIG. 24 that piston holders 700, 700' and retaining blocks 720, 720' are in a retracted position (insertion position). Thus opening slide 570 with rocker 621 is also in the retracted position. Clutch release levers 501, 501' are thus still open (however, not completely as the possibility of pre-latching must exist), as can be seen particularly in FIG. 27. FIG. 25 illustrates a cross-section along the line XXV-XXV from FIG. 24. As the retaining blocks 720, 720' are at the same height in relation to an extension direction of the spindles 470, 470', in this case the view of both retaining blocks 720, 720' is identical. Springs 710, 710' and the ends 730a, 730a', 730b, 730b' thereof (see also FIG. 22) are particularly easy to see. FIG. 26 illustrates the pump unit 200 in a view from above wherein the top side of the valve cover with the interrupter tab on rib 273 can be seen. FIG. 28 illustrates the pump unit 200 in a lateral view, wherein pressure hose 105 is clearly visible.

By moving retaining blocks 720, 720' from the reference position into the insertion position, as is illustrated in FIGS. 22 to 28, clutch release levers 501, 501' are already being actuated and axle bolts 502, 502' are moved slightly towards each other. When the operator inserts pump unit 200, the axle bolts 502, 502' positioned for pre-latching are again pushed apart slightly by cylinder block 211 (or by lateral surfaces of the cylinder block 211) such that pump unit 200 forces itself between the axle bolts 502, 502' into holding device 510. As soon as the lateral surfaces of the cylinder block 211 re-release axle bolts 502, 502', which have been pushed apart, these bolts 502, 502' are positioned on the top and bottom side of the valve covers respectively behind retaining ribs 273, 273' by moving them towards each other again (conditional on tension springs 503, 503') and pump unit 200 is pre-latched. In the insertion position, the clutch release levers 501, 501' are not yet completely closed as they only define the pre-latching condition.

By means of the signal D generated due to interruption (e.g. reflection) of the photoelectric light barrier's 901 light beam (after insertion of pump unit 200 into holding device 500), both coupling systems or coupling devices 130, 130' are activated and piston holders 700, 700' are moved forwards by way of the spindles 470, 470' from the retracted insertion position in the direction of holding device 500 into the attaching and coupling position. During travel into the attaching and coupling position, the clutch release levers 501, 501' close completely (as described above) such that pump unit 200 is accommodated firmly in holding device 500.

By moving the retaining blocks 720, 720' into the attaching and coupling position, retaining blocks 720, 720' strike against the pistons 250, 250'. The purpose of the pre-latching described above becomes apparent in this case. If pre-latching had not taken place, the retaining blocks 720, 720' would re-eject pump unit 200 out of holding device 500.

Retaining blocks 720, 720' are disposed on spindles 470, 470' and have insertion openings 770, 770', into which piston rods 250, 250' may be inserted with their coupling noses 170, 170' in the attaching and coupling position. Springs 710, 710' are attached to retaining blocks 720, 720' such that they run through retaining blocks 720, 720' and spring ends 730a, 730a', 730b, 730b' emerge on an underside of the retaining blocks 720, 720' pointing towards base plate 651 (FIG. 25). As can be seen from FIG. 22, on retaining blocks 720, 720', disposed in each case on their undersides pointing towards base plate 651, is a slide 622, 622' whereby the slides 622, 622' are each attached by way of slide axles 623, 623' to a front side of retaining blocks 720, 720' pointing towards the holding device 500. The slides 622, 622' are movable by way of retaining blocks 720, 720' with and over slide axles 623, 623' relative to the retaining blocks 720, 720'. This means that retaining blocks 720, 720' and slides 622, 622' may be moved in relation to one another.

Figure 44:
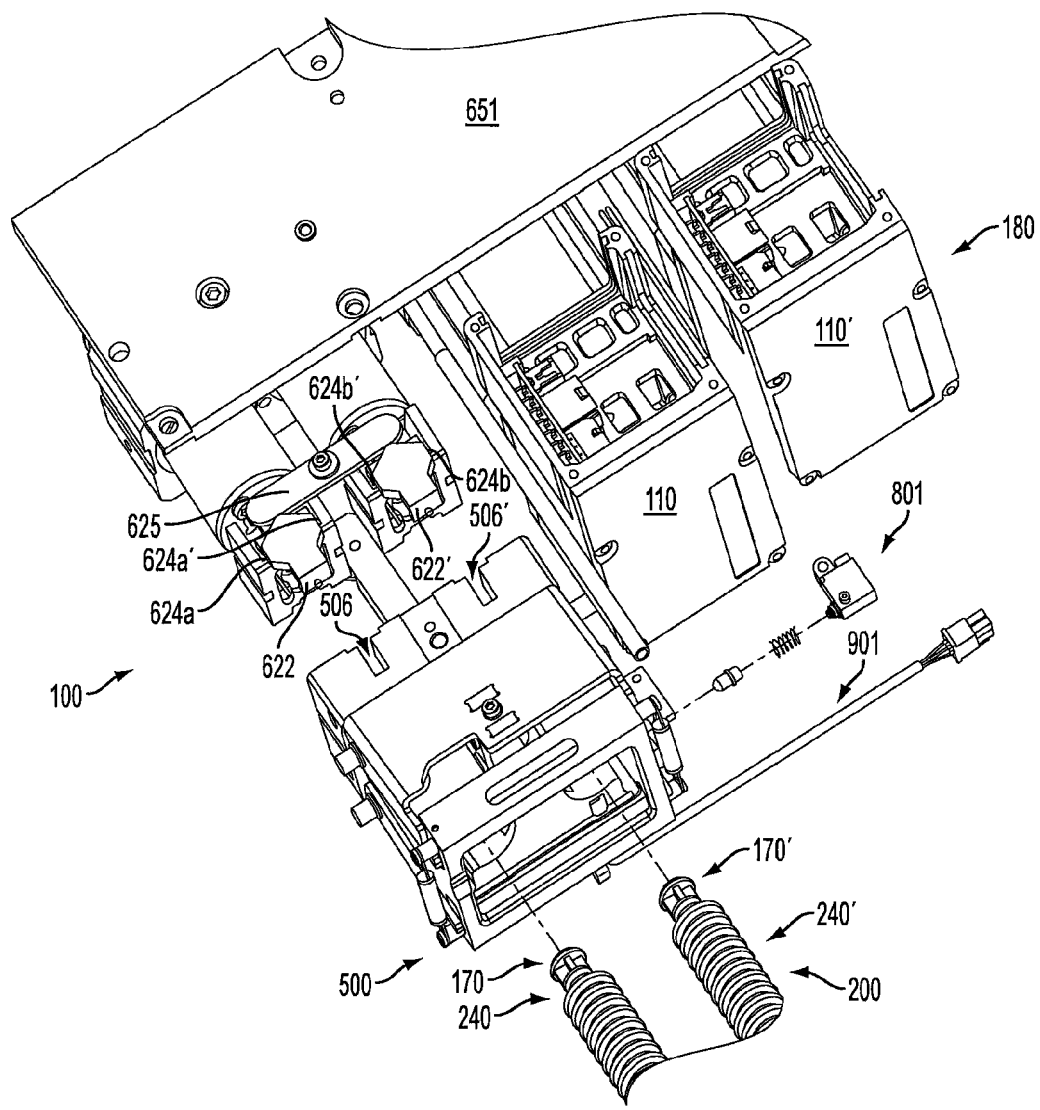
FIG. 44 illustrates a perspective view of the pump actuating device, shown from below, not yet coupled with a pump unit.

By moving the piston holders 700, 700' and therefore the retaining blocks 720, 720' further forwards into the attaching and coupling position, slides 622, 622' are picked up with retaining blocks 720, 720' and eventually strike against a rear side, pointing towards piston holders 700, 700', of holding device 500 or retaining device 510. FIG. 44 shows pump actuating device 100 from underneath. Here both slides 622, 622' are also discernible. Retaining device 510 is configured such that it can accommodate the slides 622, 622', at least in part, on the rear side. Thus, for example, cut-outs 506, 506' are provided, which accommodate slide axles 623, 623' on one hand but also a rear end of the slide 622, 622' itself. Basically, it is sufficient to embody the cut-outs such that the slide axes 623, 623' may be pushed in so that the slides 622, 622' can be supported against the back side of the retaining device 510.

As can be seen in particular from FIG. 44, slides 622, 622' are configured such that they cross, aligned with the direction of the spindle 470, 470', from a widening region to a region of maximum width and from this back to a tapering region (similar to a diamond shape or more similarly to a benzene ring shape). The slides 622, 622' accordingly have expansion surfaces 624a, 624', 624b, 624b'. In the still uncoupled condition (pistons 250, 250' are not coupled to piston holders 700, 700'), the regions of maximum width engage respectively with their expansion surfaces 624a, 624a' and 624a, 624b' between spring ends 730a, 730a' and 730b, 730b' of springs 710, 710' and keep the springs 710, 710' extended and thus "open". Piston holders 700, 700' are moved by means of the travelling motion described above via the spindles 470,

470' towards pistons 250, 250' of pre-latched pump unit 200 in such a way that pistons 250, 250' are pushed into insertion openings 770, 770'. At the same time or when the pistons 250, 250' have been received in the retaining blocks 720, 720', the slides 622, 622' are supported against the rear side of retaining device 510 or holding device 500 such that the spring ends 730a, 730a', 730b, 730b' clamped over the regions of maximum width of the slides 622, 622' slip over the expansion surfaces 624a, 624a', 624b, 624b' onto the tapering region of the slides 622, 622' and thus snap together behind coupling noses 170, 170' of pistons 250, 250'. Coupling noses 170, 170' are tapered at their ends for easier insertion. After insertion of coupling noses 170, 170' into piston holders 700, 700', piston rods 250, 250' are firmly connected—resistant to pulling and pushing—to piston holders 700, 700' and to retaining blocks 720, 720'. At this point, the clutch release levers 501, 501' are also completely closed because the plain bearings 573, 573' of the opening slides 570 are not in contact on the opening ramps 550, 550' or are only in contact in the lower regions thereof.

Pump unit 200 now fully latched (clutch release levers 501, 501' closed, pistons 250, 250' coupled) with coupled pistons 250, 250' is now ready for operation. Pump operation is made clear by way of FIGS. 29 to 33. As already described in greater detail above, pump operation takes place by means of alternating movement of spindles 470, 470' and therefore of pistons 250, 250'. Pistons 250, 250' and spindles 470, 470' are visible in FIG. 30. The bellows are not illustrated in this case.

Figure 29:
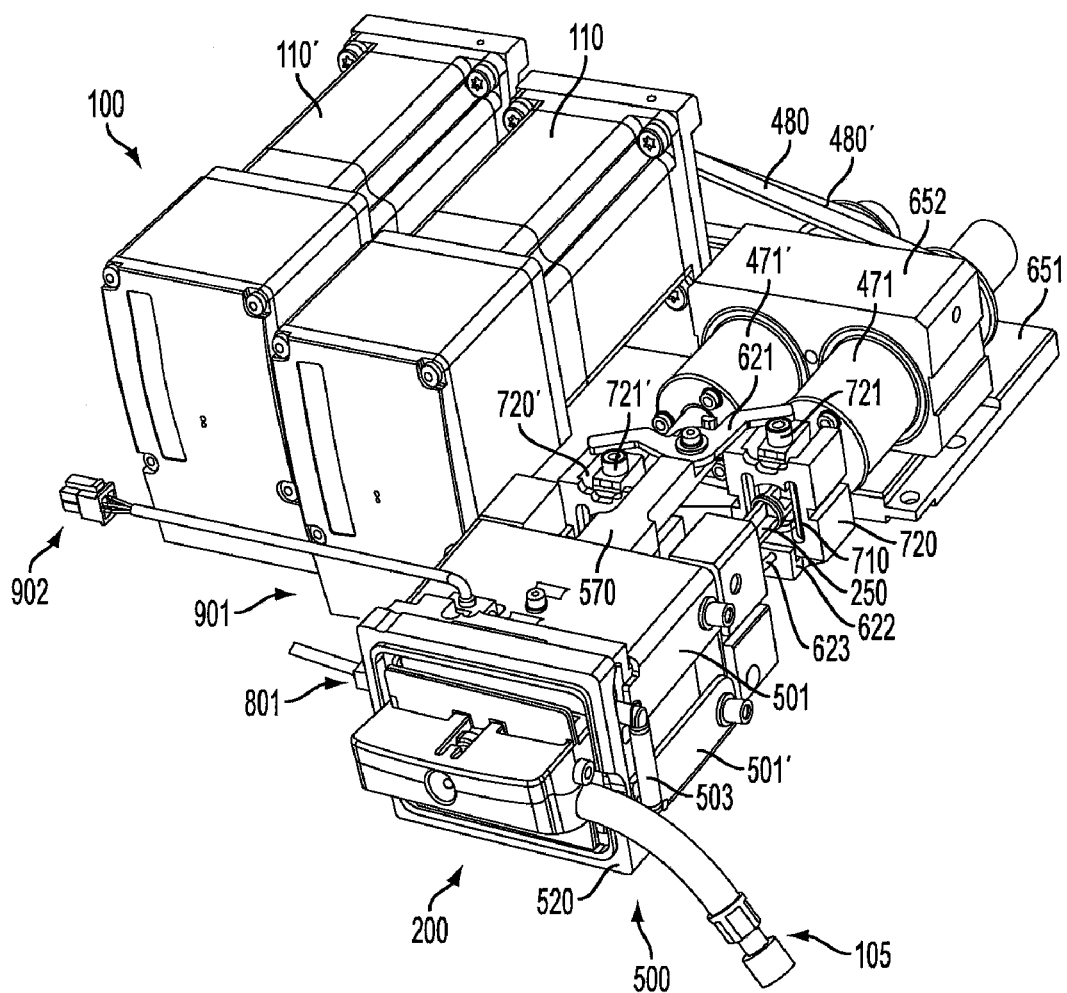
FIG. 29 illustrates a perspective view of the pump actuating device coupled with a pump unit in operation.

FIG. 29 illustrates the medical pump in its entirety, that is to say pump actuating device 100 with inserted pump unit 200.

Figure 30:
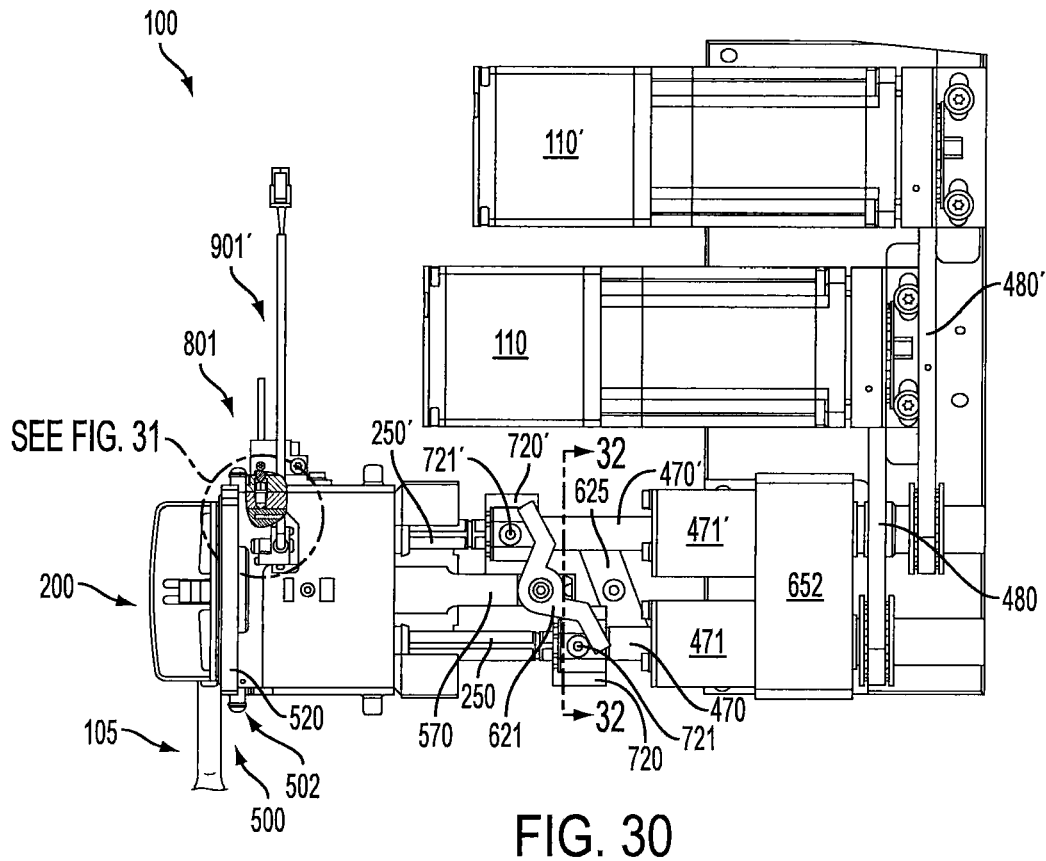
FIG. 30 illustrates a view from above of the pump actuating device coupled with a pump unit according to FIG. 29.

It can also be seen from FIG. 30 that rocker 621 is moved in a rocking manner in alternating operation of the pump and thus does not actuate opening slide 570. Thus opening slide 570 remains in the position in which clutch release levers 501, 501' are completely closed.

Figure 32:
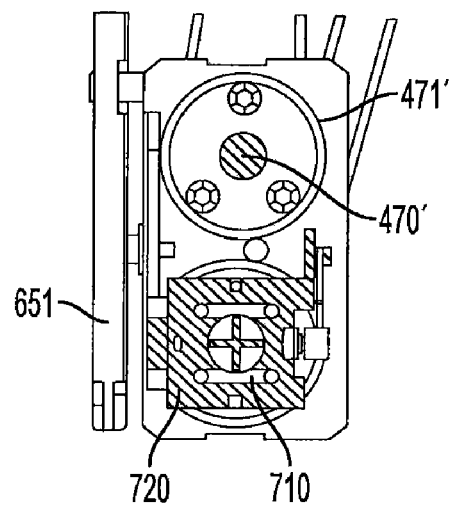
FIG. 32 illustrates a cross-section along the line XXII-XXII from FIG. 30.

FIG. 32 illustrates a cross-section along the line XXXII-XXXII from FIG. 30. Spindle holder 471' with spindle 470' is visible and retaining block 720 is shown in cross-section. From the cross-section it becomes clear that the piston holders 700, 700' are not at the same height in relation to an extension direction of the spindles 470, 470'.

Figure 31:
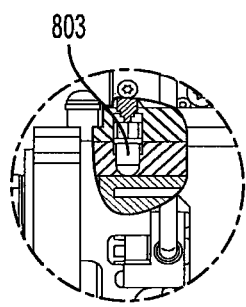
FIG. 31 illustrates an enlarged detail view from FIG. 30.

FIG. 31 illustrates a detail from FIG. 30, specifically actuated microswitch 801, wherein actuating pin 801 is depressed.

Figure 33:
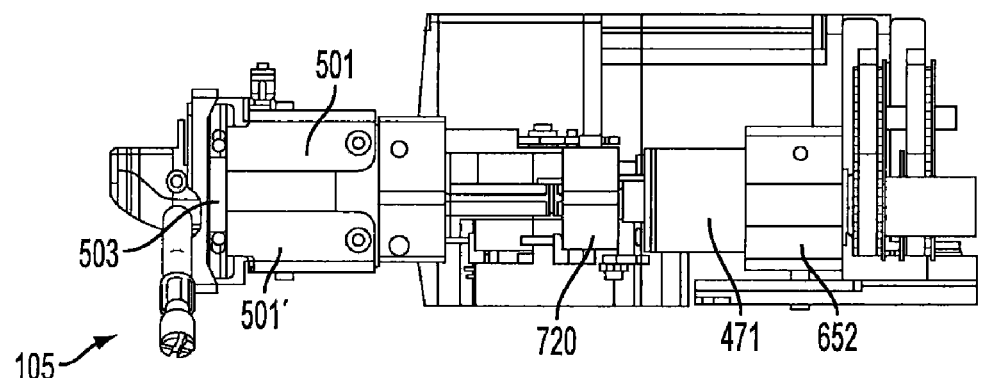
FIG. 33 illustrates a lateral view of the pump actuating device coupled with a pump unit according to FIG. 29.

FIG. 33 illustrates the arrangement according to FIG. 30 in a lateral view. In this case it can be seen that clutch release levers 501, 501' are completely closed in pump operation.

Removal of pump unit 200 from pump actuating device 100 will now be described referring to FIGS. 34 to 36.

An operator B must supply an appropriate signal to motor control system 150 for the purpose of removal. This takes place by releasing or actuating the manual or foot switch (not illustrated) and actuation of, for example, the eject button. As soon as the manual or foot switch is released, the spindles 470, 470' and therefore the pistons 250, 250' stop in the position they are in at the moment, i.e. they react immediately to the shutdown signal. Only in this way is it possible to prevent any fluid from continuing to be supplied to the corresponding point via the applicator.

Via the further signal, e.g. actuation of a further switch (eject button), an unlatching process is triggered by motor control system 150. It should be noted here that in practice a type of touch screen is usually used (as already explained above). Thus actuation of a switch is also to be understood as touching of a corresponding area on the screen.

The motors 110, 110' drive the spindles 470, 470' and therefore retaining blocks 720, 720' with the pistons 250, 250' still coupled up backwards into the detaching and uncoupling position (in principle this is the reference position). In this case, as soon as the retaining blocks 720, 720' have reached their rear position, slides 622, 622' strike against a further rocker 625, which is disposed on a rib embodied between spindle holders 471, 471' and joined to the base plate 651, and which is identifiable in particular in FIG. 44. This rocker 625, which in "normal" pump operation likewise moves back and forth with the pistons 250, 250' (in order not to activate the slides 622, 622'), serves as a further limit stop for slides 622, 622'. The slides 622, 622' strike against the rocker 625 (due to the fact that both slides strike against rocker 625, it is unable to move out of the way) and are displaced over slide axle 623, 623' towards the pistons 250, 250' such that the slides 622, 622' again push with their broadsides between spring ends 730a, 730a', 730b, 730b' and are able to expand springs 710, 710'. In principle, retaining block 720, 720' and slide 622, 622' are displaced relative to one another on contact with the rocker 625 (they are moved away from one another) depending on the position of the individual retaining blocks 720, 720'. As a result, coupling noses 170, 170' of pistons 250, 250' are released. Due to the rocker-like concurrent motion of rocker 625, it is not able to act as a limit stop for the slides 622, 622' during normal pump operation. As a result it is not possible for the slides 622, 622' to engage in the spring ends 730a, 730a', 730b, 730b' and unlatch the pistons 250, 250'.

Simultaneous with travelling backwards towards the spindle holders 471, 471', that is to say into the detaching and uncoupling position, the clutch release levers 501, 501' open (the retaining blocks 720, 720' pick up rocker 621 and therefore opening slide 570 and carry it backwards). However, the mechanism is embodied in such a way that complete opening of the clutch release levers 501, 501' only takes place when pistons 250, 250' are already uncoupled from retaining blocks 720, 720'. A pre-latching stage is no longer provided for here. The sequence of uncoupling and unlatching specified here (first uncoupling of the pistons 250, 250', then unlatching of the holding device 500) is preferably provided so that the operator B can only actively remove the pump unit 200 from the holding device 500 when the pistons 250, 250' are uncoupled. Otherwise, the operator B would possibly pull on the pump unit 200 located in the opened holding device 500 wherein uncoupling of the pistons 250, 250' has not yet taken place. This would possibly lead to the pump system being damaged.

The operator B can then remove pump unit 200 from pump actuating device 100 without a problem. As soon as the pump unit 200 has actually been removed, actuating pin 803 of microswitch 801 is released (the microswitch 801 is deactivated) because cylinder block 211 (or the side wall) no longer presses on the actuating pin 803. The signal thus generated, second detection signal D', is transmitted to motor control system 150 such that the motors 110, 110' move piston holders 700, 700' and retaining blocks 720, 720' into the position which enables a new pump unit 200 to be inserted (insertion position). As a result pump actuating device 100 would be ready for insertion of a new pump unit 200. In this insertion position, the pump actuating device 100 is in the idle state.

Figure 34:
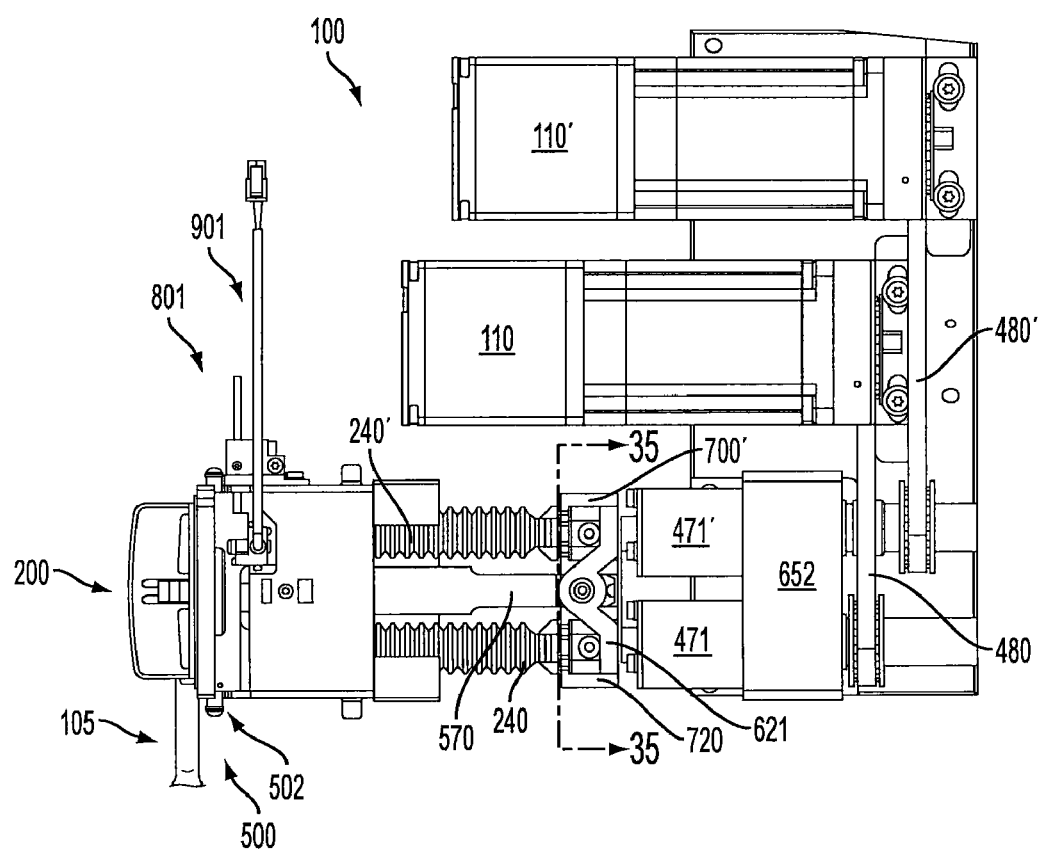
FIG. 34 illustrates a view from above of the pump actuating device coupled with a pump unit.

FIG. 34 illustrates pump unit 200 still coupled to pump actuating device 100 from above. Retaining blocks 720, 720' are in the retracted position, opening slide 570 is likewise pulled to the rear with rocker 621 such that, as can be seen from FIG. 36, clutch release levers 501, 501' are completely opened for removal of pump unit 200.

Figure 35:
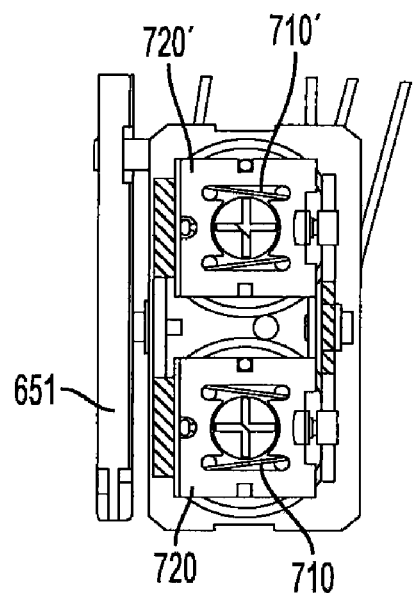
FIG. 35 illustrates a cross-section along the line XXXV-XXXV from FIG. 34.
Figure 36:
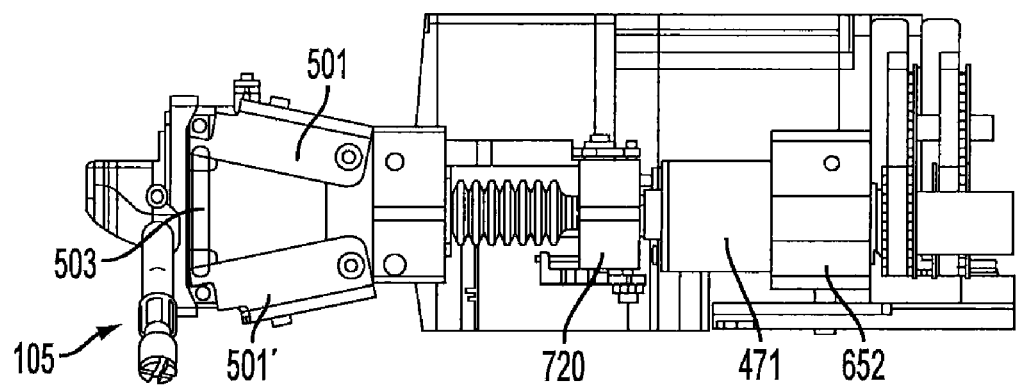
FIG. 36 illustrates a lateral view of the pump actuating device coupled with a pump unit according to FIG. 34.

FIG. 35 illustrates a cross-section along the line XXXV-XXXV from FIG. 34. As apparent from the cross-section, for uncoupling, the retaining blocks 720, 720' are at the same height in relation to the extension direction of the pistons 250, 250'.

FIG. 37 illustrates pump actuating unit 100, whereby piston holders 700, 700' are in the reference position by means of motors 110, 110'. Even if the insertion position and reference position appear to be almost identical according to the diagrams, it should be pointed out that the retaining blocks 720, 720' are positioned differently in the respective positions.

Figure 24:
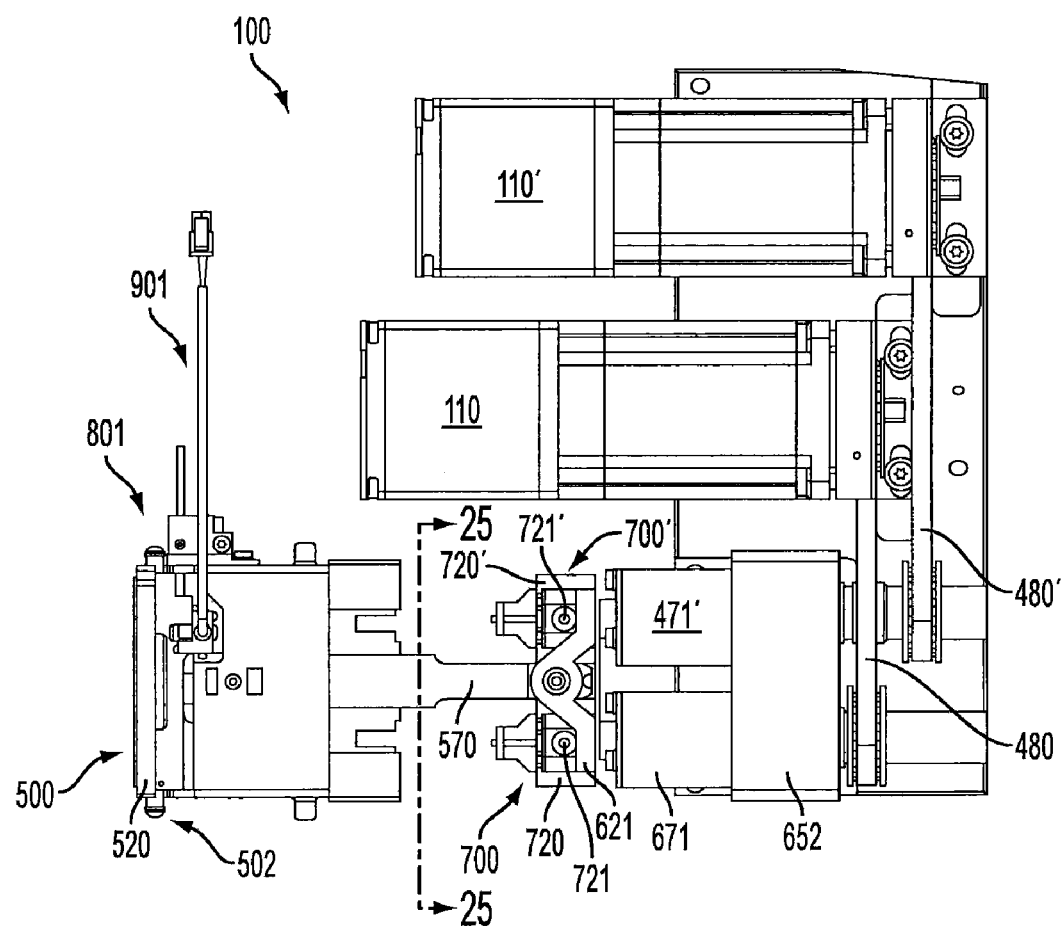
FIG. 24 illustrates a view from above of the pump actuating device according to FIG. 22.
Figure 38:
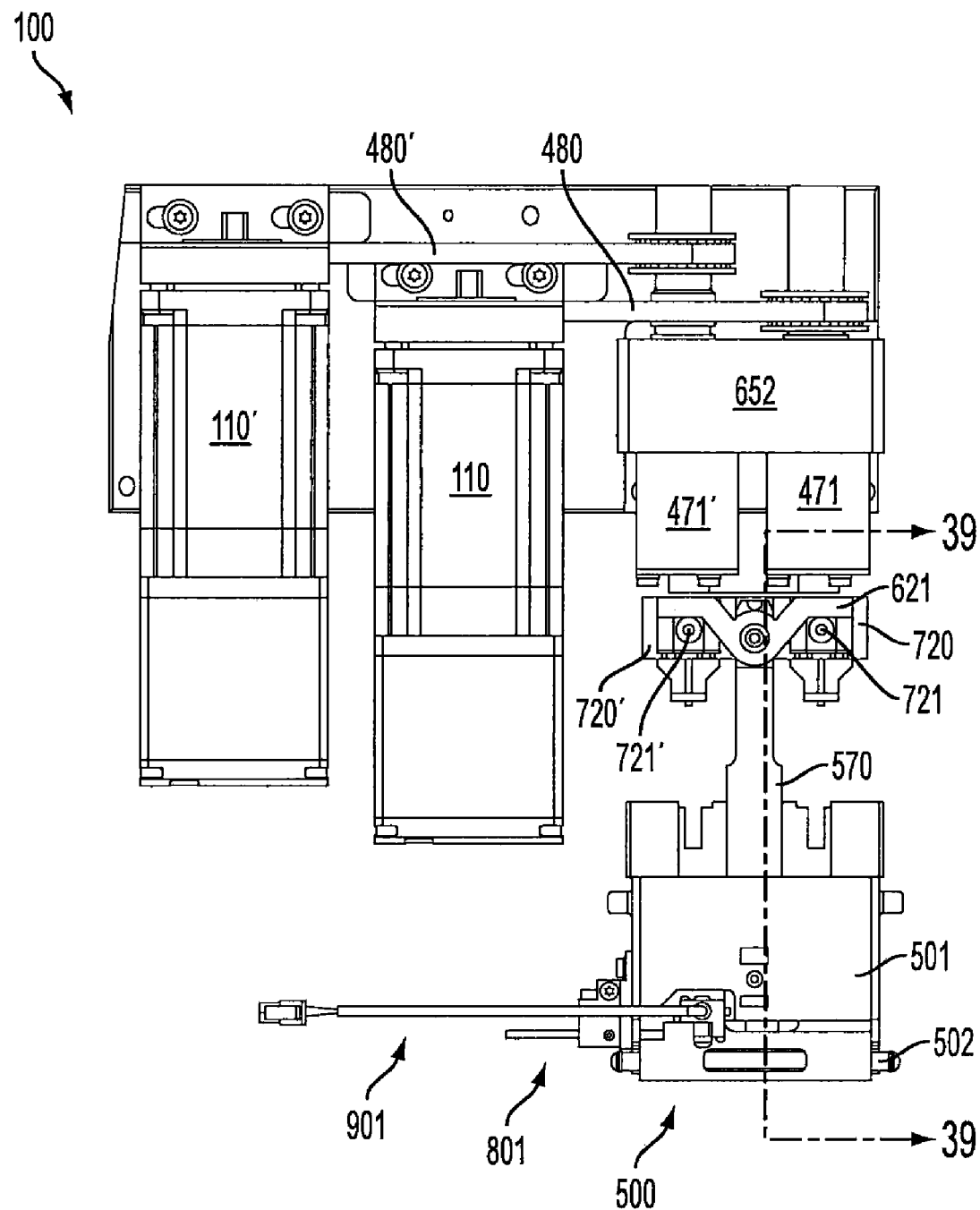
FIG. 38 illustrates an enlarged view of the pump actuating device coupled with a pump unit according to FIG. 24.

FIG. 38 illustrates a somewhat magnified view of the pump actuating device 100 with coupled up pump unit 200, as it has already been demonstrated in FIG. 24. FIG. 39 illustrates a cross-section along the line XXXIX-XXXIX from FIG. 38. In this case, opening slide guide 571 is visible. Opening slide 570 is located with rocker 621 above retaining blocks 720, 720' in the retracted insertion position. To this extent, plain bearings 573, 573' are located at the highest level of opening ramps 550, 550' and clutch release levers 501, 501' are opened.

Figure 40:
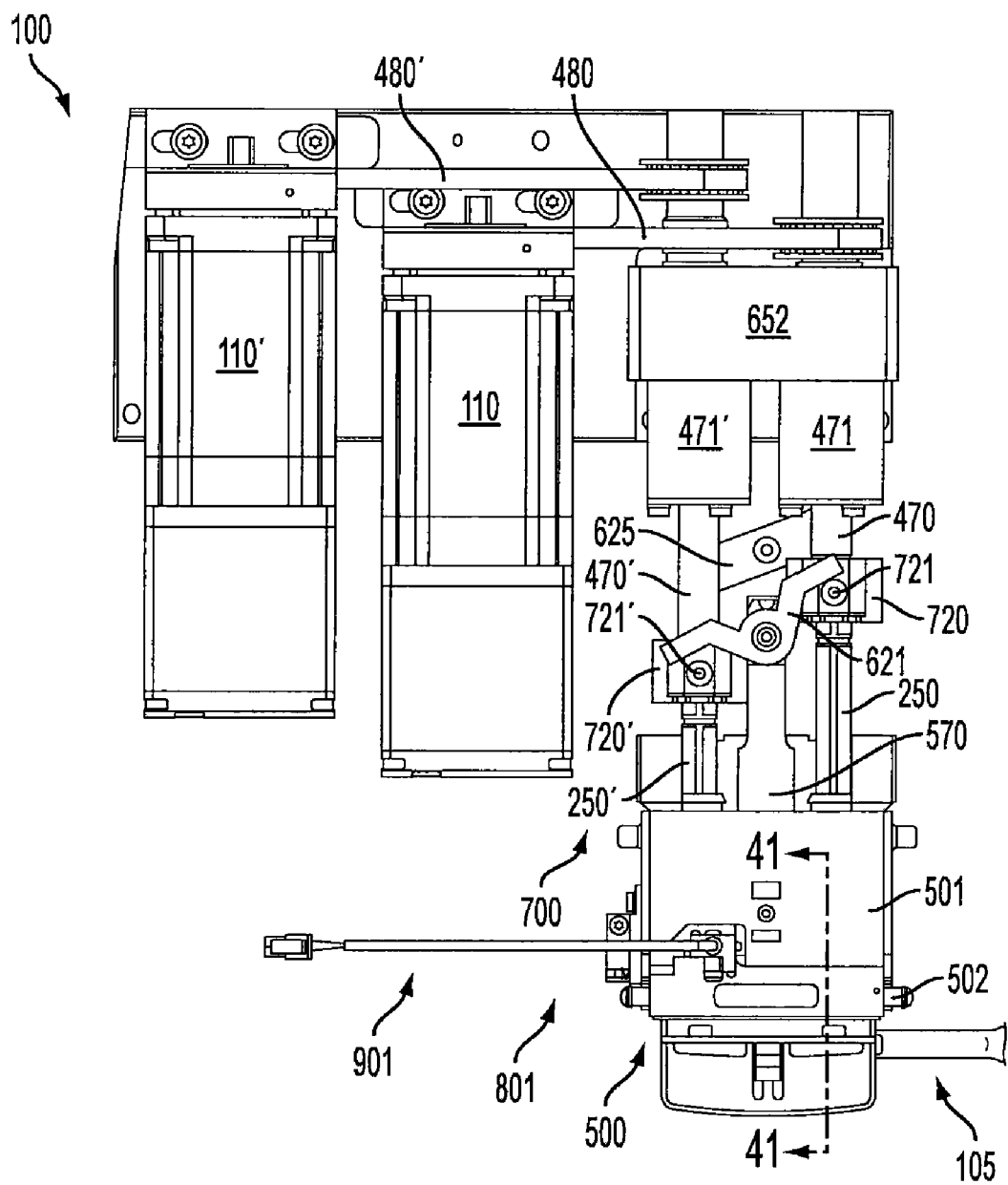
FIG. 40 illustrates an enlarged view of the pump actuating device coupled with a pump unit according to FIG. 30.
Figure 41:
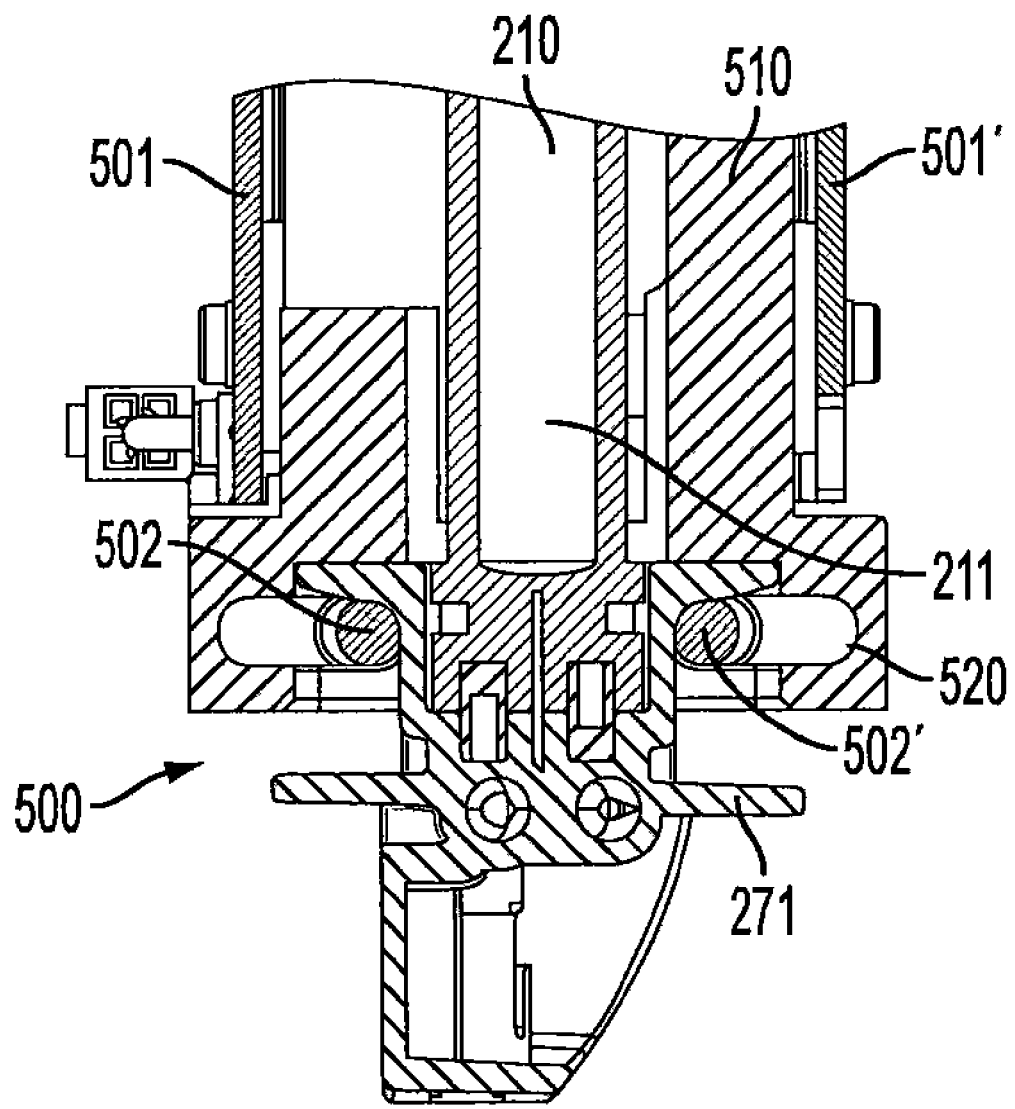
FIG. 41 illustrates a cross-section along the line XLI-XLI from FIG. 40.

FIG. 40 illustrates a somewhat enlarged view of the pump actuating device 100 with coupled up pump unit 200 according to FIG. 30. FIG. 41 illustrates a cross-section along the line XLI-XLI from FIG. 40. In this case, with pump unit 200 pushed into holding device 500, the cross-section through a cylinder 210 is illustrated as a component part of cylinder block 211. Axle bolts 502, 502' are brought together as closely as possible as the clutch release levers 501, 501' closed.

Both the photoelectric barrier 901 and also the microswitch 801 (or micro pushbutton) generate signals which are transmitted to the motor control system or control system 150. On inserting the pump unit 200 into the pump actuating device 100, there is, however, particular provision for the signal generated due to activation of the photoelectric barrier 901 to be evaluated by way of the control system 150 and essentially for only this signal to indicate that a pump unit 200 ready for attaching and coupling has been inserted. As soon as the pump unit 200 has been inserted in the pump actuating device 100 in such a way that the photoelectric barrier 901 is "activated", that is the light beam is interrupted or reflected, a predetermined relative position between the pump unit 200 and the pump actuating unit 100 is reached—it is thus indicated that a pump unit 200 has been inserted—and the signal, first detection signal D, initiates activation of the motors 110, 110' for finally moving the retaining blocks 720, 720' via the spindles 470, 470'. The attaching and coupling position and, if appropriate, the standby position are approached on the basis of this signal. Pump operation can then be initiated from this position. As soon as pump operation is interrupted and desired removal of the pump unit 200 used is indicated, the retaining blocks 720, 720' are moved into the detachment and uncoupling position. The microswitch 801 is deactivated on removing the pump unit 200 from the holding device 500 and the signal thus generated and transmitted to the control system 150, second detection signal D', causes the control system 150 to activate the motors 110, 110' such that the retaining blocks 720, 720' are moved into the insertion position. A new pump unit may be inserted. The insertion position is to be understood in principle as an idle state or readiness state.

Due to the sensors, i.e. due to the detection means, in particular attaching and coupling of the pump unit 200 to the pump actuating device 100 and therefore creation of a working condition of the medical pump are automatically initiated by the system. Positioning of the pump actuating device 100 in the insertion position following a preceding use may also be performed automatically in these embodiments, in this case for example due to deactivation of the microswitch 801 or micro pushbutton.

If necessary, it would be possible to initiate attaching and coupling only if at least two detection means transmit a signal D' to the control system 150 such that this signal only activates the motors 110, 110' if both signals are communicated. In the embodiments illustrated above, however, the primary provision is to evaluate only the photoelectric barrier signal 901 as a detection signal for attaching and coupling.

It should be pointed out here that all the above described parts and in particular the details illustrated in the drawings are essential for the disclosed embodiments alone and in combination. Adaptations thereof are the common practice of persons skilled in the art.

The invention claimed is:

1. A medical pump for use in water jet surgery, the medical pump comprising:
   a pump unit having two pistons disposed within respective cylinders; and
   a pump actuating device, the pump actuating device comprising:
   a holding device configured to attach and detach the pump unit respectively to and from the pump actuating device;
   coupling devices configured to couple and uncouple respective pistons to and from the pump actuating device;
   a drive device controlled by a control system to actuate the pump unit by alternately displacing the two pistons within respective cylinders, to open and/or close the holding device, and to open and/or close the coupling devices; and
   a detection device in communication with the control system that detects a relative position between the pump unit and the pump actuating device and, when the pump unit is inserted into the pump actuating device, transmits a first detection signal to the control system and when the pump unit is not inserted into the pump actuating device, transmits a second detection signal to the control system,
   wherein upon receiving the first detection signal, the control system controls the drive device to close the holding device and the coupling device such that the pump unit is attached to and the pistons are coupled to the pump actuating device,
   wherein the detection device further comprises a photoelectric barrier and the pump unit further comprises an interrupter device for interrupting a light beam of the photoelectric barrier, thereby causing the detection device to transmit the first detection signal, and
   wherein the detection device further comprises a pushbutton or switch device that transmits the second detection signal.

2. The medical pump according to claim 1, further comprising at least one input element in communication with the control system that transmits an input signal to the control system, wherein upon receiving the input signal, the control system controls the drive device to open the holding device and the coupling devices such that the pump unit is detached from and the at least one piston is uncoupled from the pump actuating device.

3. The medical pump according to claim 1, wherein upon receiving the second detection signal, the control system controls the drive device to generate a state which allows the insertion of a new pump unit.

4. The medical pump according to claim 1, wherein the photoelectric barrier is a forked light barrier.

5. The medical pump according to claim 1, wherein the photoelectric barrier responds to reflection of light emitted by a transmitter of the photoelectric barrier to generate the first detection signal.

6. The medical pump according to claim 1, wherein the pushbutton device is a micro pushbutton.

7. The medical pump according to claim 1, wherein the switch device is a microswitch.

8. The medical pump according to claim 1, wherein the pump actuating device further comprises first snap-in connection devices and the pump unit further comprises second snap-in connection devices, wherein attachment and detachment of the pump unit respectively to and from the pump actuating device is effected, respectively, by engagement of the first and second snap-in connection devices with each other and by disengagement from each other.

9. The medical pump according to claim 1, wherein the pump actuating device further comprises first snap-in connection devices and the pump unit further comprises second snap-in connection devices, wherein coupling and decoupling of the pistons respectively to and from the pump actuating device is effected, respectively, by engagement of the first and second snap-in connection devices with each other and by disengagement from each other.

10. The medical pump according to claim 8, wherein the first snap-in connection devices are axle bolts of the holding device.

11. The medical pump according to claim 10, wherein the second snap-in connection devices are retaining ribs on a valve cover, and wherein the axle bolts cooperate with the retaining ribs when the holding device is closed.

12. The medical pump according to claim 8, wherein the first snap-in connection devices are claws on the holding device.

13. The medical pump according to claim 12, wherein the second snap-in connection devices are retaining noses on a cylinder head of the cylinders, and wherein the claws cooperate with the retaining noses when the holding device is closed.

14. The medical pump according to claim 9, wherein the first snap-in connection devices are retaining blocks and associated springs of the at least one coupling device.

15. The medical pump according to claim 14, wherein the second snap-in connection devices are coupling noses on ends of the pistons, and wherein the retaining blocks and associated springs cooperate with the coupling noses when the coupling device is closed.

16. The medical pump according to claim 8, wherein closing of the holding device is accomplished by automatic snapping of the first and second snap-in connection devices performed by the drive device at the control of the control system and wherein opening of the holding device is accomplished by automatic opening of the first and second snap-in connection devices performed by the drive device at the control of the control system.

17. The medical pump according to claim 9, wherein closing of the coupling device is accomplished by automatic snapping of the first and second snap-in connection devices performed by the drive device at the control of the control system and wherein opening of the coupling device is accomplished by automatic opening of the first and second snap-in connection devices performed by the drive device at the control of the control system.

18. The medical pump according to claim 1, wherein the drive device comprises a linear drive having at least one spindle and at least one motor for driving the spindle.

19. The medical pump according to claim 1, wherein the control system controls the drive device to cause displacement of the pistons at a constant speed.

20. The medical pump according to claim 1, wherein the drive device comprises two motors, whereby, for purposes of opening or closing of the holding device and/or the coupling devices, the drive device may deviate from alternating operation of the pistons.

21. The medical pump according to claim 1, wherein the drive device comprises a motor having gears, whereby, for purposes of opening or closing of the holding device and/or the coupling devices, the drive device may deviate from alternating operation of the pistons.

* * * * *